US011427648B2

United States Patent
Blot-Chabaud et al.

(10) Patent No.: US 11,427,648 B2
(45) Date of Patent: Aug. 30, 2022

(54) ANTI-CD146 ANTIBODIES AND USES THEREOF

(71) Applicants: UNIVERSITE D'AIX-MARSEILLE, Marseilles (FR); INSERM (INSTITUT NATIONAL DE LA SANTÉ ET DE LA RECHERCHE MÉDICALE), Paris (FR); ASSISTANCE PUBLIQUE HÔPITAUX DE MARSEILLE, Marseilles (FR)

(72) Inventors: Marcel Blot-Chabaud, Fuveau (FR); Benjamin Guillet, Aix en Provence (FR); Marie Nollet, Frejus (FR); Jimmy Stalin, Lausanne (CH); Nathalie Bardin, Marseilles (FR); Françoise Dignat-George, Marseilles (FR)

(73) Assignees: UNIVERSITE D'AIX-MARSEILLE, Marseilles (FR); ASSISTANCE PUBLIQUE HÔPITAUX DE MARSEILLE, Marseilles (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 126 days.

(21) Appl. No.: 16/652,079

(22) PCT Filed: Oct. 5, 2018

(86) PCT No.: PCT/EP2018/077073
§ 371 (c)(1),
(2) Date: Mar. 30, 2020

(87) PCT Pub. No.: WO2019/068842
PCT Pub. Date: Apr. 11, 2019

(65) Prior Publication Data
US 2020/0262929 A1 Aug. 20, 2020

(30) Foreign Application Priority Data
Oct. 6, 2017 (EP) .................................... 17306348

(51) Int. Cl.
*C07K 16/30* (2006.01)
*A61P 35/00* (2006.01)
*A61K 51/10* (2006.01)
*A61K 39/00* (2006.01)

(52) U.S. Cl.
CPC ...... *C07K 16/3092* (2013.01); *A61K 51/1045* (2013.01); *A61P 35/00* (2018.01); *A61K 2039/505* (2013.01)

(58) Field of Classification Search
CPC ........... C07K 16/3092; A61K 51/1045; A61K 2039/505; A61P 35/00
See application file for complete search history.

(56) References Cited

U.S. PATENT DOCUMENTS

| | | | | | |
|---|---|---|---|---|---|
| 4,208,479 | A | * | 6/1980 | Zuk | C07J 41/0016 435/7.9 |
| 10,774,153 | B2 | * | 9/2020 | Blot-Chabaud | A61P 17/00 |
| 2006/0246077 | A1 | * | 11/2006 | Bar-Eli | C07K 16/3092 424/155.1 |

FOREIGN PATENT DOCUMENTS

WO    WO 03/057006    7/2003

OTHER PUBLICATIONS

Wang et al., CD146, a multi-functional molecule beyond adhesion, Cancer Letters 330, 150-162, Publication Date: Dec. 20, 2012 (Year: 2012).*
Rudikoff et al., Single amino acid substitution altering antigen-binding specificity, PNAS, USA, 1982, 79: 1979-1983 (Year: 1982).*
Yang et al., Targeting CD146 with a 64Cu-labeled antibody enables in vivo immunoPET imaging of high-grade gliomas, PNAS, E6525-E6534, Publication Date: Nov. 9, 2015 (Year: 2015).*
Hernandez, R. et al. "ImmunoPET Imaging of CD146 Expression in Malignant Brain Tumors" *Molecular Pharmaceutics*, Jun. 2016, pp. 2563-2570, vol. 13, No. 7.
Mills, L. et al. "Fully Human Antibodies to MCAM/MUC18 Inhibit Tumor Growth and Metastasis of Human Melanoma" *Cancer Research*, Sep. 1, 2002, pp. 5106-5114, vol. 62.
Nodomi, S. et al. "CD146 is a novel marker for highly tumorigenic cells and a potential therapeutic target in malignant rhabdoid tumor" *Oncogene*, 2016, pp. 5317-5327, vol. 35, No. 40.
Nollet, M. et al. "A novel anti-CD146 antibody specifically targets cancer cells by internalizing the molecule" *Oncotarget*, 2017, pp. 112283-112296, vol. 8, No. 68.
Stalin, J. et al. "Therapeutic and Diagnostic Antibodies to CD146: Thirty Years of Research on Its Potential for Detection and Treatment of Tumors" *Antibodies*, 2017, pp. 1-13, vol. 6, No. 17.
Zhang, Y. et al. "Generation and Characterization of a Panel of Monoclonal Antibodies Against Distinct Epitopes of Human CD146" *Hybridoma*, 2008, pp. 345-352, vol. 27, No. 5.
Written Opinion in International Application No. PCT/EP2018/077073, dated Jan. 9, 2019, pp. 1-10.

* cited by examiner

*Primary Examiner* — Peter J Reddig
*Assistant Examiner* — Cheng Lu
(74) *Attorney, Agent, or Firm* — Saliwanchik, Lloyd & Eisenschenk

(57) ABSTRACT

The present invention relates to the field of diagnostic and treatment of cancer, particularly melanoma, pancreatic cancer, kidney cancer and colon cancer. In particular, the invention relates to an antibody directed specifically to CD146-positive tumors and its applications, particularly for use as a medicament for the prevention and/or treatment of cancer, for use in a method of diagnostic or prognostic of a cancer, or for use as a radiotracer when labelled with a radioactive element.

19 Claims, 5 Drawing Sheets
Specification includes a Sequence Listing.

| Applicant's or agent's File reference B2605PC00 | International application No. PCT/EP2018/077073 |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description
on page 10 , line 27,28,29 .

B. IDENTIFICATION OF DEPOSIT    Further deposits are identified on an additional sheet ☐

Name of depositary institution
COLLECTION NATIONALE DE CULTURES DE MICROORGANISMES (CNCM)

Address of depositary institution (including postal code and country)
INSTITUT PASTEUR
25 rue du Docteur Roux
75724 PARIS CEDEX 15

| Date of deposit | Accession Number |
|---|---|
| October 4, 2017 | CNCM I-5246 |

C. ADDITIONAL INDICATIONS (leave blank if not applicable)    This information is continued on an additional sheet ☐

D. DESIGNATED STATES FOR WHICH INDICATIONS ARE MADE (if the indications are not for all designated States)

E. SEPARATE FURNISHING OF INDICATIONS (leave blank if not applicable)
The indications listed below will be submitted to the International Bureau later (specify the general nature of the indications e.g., "Accession Number of Deposit")

| For receiving Office use only | For International Bureau use only |
|---|---|
| ☒ This sheet was received with the international application | ☐ This sheet was received by the International Bureau on: |
| Authorized officer Kuiper-Cristina, Nathalie | Authorized officer |

Form PCT/RO/134 (July1998; reprint Janu)

FIG. 4

ANTI-CD146 ANTIBODIES AND USES THEREOF

CROSS-REFERENCE TO RELATED APPLICATION

This application is the U.S. national stage application of International Patent Application No. PCT/EP2018/077073, filed Oct. 5, 2018.

The Sequence Listing for this application is labeled "Seq-List.txt" which was created on Mar. 27, 2020 and is 36 KB. The entire content of the sequence listing is incorporated herein by reference in its entirety.

FIELD OF THE INVENTION

The present invention relates to the field of diagnostic and treatment of cancer, particularly cancer wherein cancer cells express CD146, such as melanoma, pancreatic cancer, kidney cancer and colon cancer.

In particular, the invention relates to an isolated antibody or a fragment thereof directed specifically against CD146-positive tumors and uses thereof. The herein described antibody as well as any fragment thereof is typically for use as a medicament, and is in particular for use for preventing or treating cancer in a subject, for use for diagnosing and/or establishing the prognostic of a cancer in a subject, or for use as a radiotracer when labelled with a radioactive element.

BACKGROUND OF THE INVENTION

Early detection and treatment of cancer is a major issue of public health. In order to efficiently fight the disease, personalized diagnosis and therapy are developed. This is based on the knowledge of the different proteins which are modified or involved in the development of the pathology. Among them, CD146 has been described to be neo-expressed in numerous tumors and to be associated with a bad prognosis.

CD146 (also identified as MCAM, Mel-CAM, MUC18, Gicerin, S-endo1) is a transmembrane glycoprotein of about 110 kDa (Shih et al., 1999). This adhesion molecule belongs to the immunoglobulin superfamily, displays five extracellular domains of the V-V-C2-C2-C2 type, a transmembrane domain and a short intracytoplasmic domain (Sers et al., 1993). Two different isoforms of the membranous CD146 have been identified that differ by their cytoplasmic tail. The CD146 molecule was initially discovered in human melanoma cells (Lehmann et al., 1989) and was then described in many other tumors such as pancreas (Maitra et al., 2003), kidney (Ueno et al., 2011), prostate (Wu et al., 2005) or breast (Zeng et al., 2011) cancer. Recently it has been showed that it was also expressed on the whole vascular endothelium (Bardin et al., 2001). In addition, CD146 was described on other cell types such as myofibroblasts, smooth muscle cells, activated T lymphocytes, Schwann cells, and extravillous trophoblasts (Shih et al., 1999; Bardin et al., 1996, Bardin et al., 2003). In cancer cells, CD146 is involved in tumor growth and dissemination (Wang et al., 2013). In particular, its expression was shown to induce epithelio-mesenchymal transition (Imbert et al., 2012). In contrast, in endothelial cells, CD146 is essentially present at the cellular junction and is involved in various physiological functions, such as permeability and leucocytes transmigration during inflammation (Bardin et al., 2003, Bardin et al., 2009).

CD146-positive tumors are characterized by a high proliferation rate and a high ability to disseminate. This is due, in particular, to the role of CD146 in epithelio-mesenchymal transition (Imbert et al., 2012). Many tumors neo-express CD146, in particular melanoma, prostatic, breast, lung, pancreatic, kidney, gastric and hepatic cancers. However, CD146 is not only expressed in these cancer cells, but is also physiologically expressed by different types of cells, essentially by endothelial and smooth muscle cells constituting the vessels (Bardin et al., 2001), and by some activated T cells (Pickl et al., 1997). In endothelial cells, CD146 is of major importance since it is essentially expressed at the junction of the cells and is involved in vascular permeability, inflammation and angiogenesis (Bardin et al., 2003; Bardin et al., 2009; Kebir et al., 2010). In smooth muscle cells, CD146 is involved in the interaction with endothelium (Shih et al., 1999). Finally, in Th17 cells, CD146 displays a major role in lymphocyte extravasation to the central nervous system (Duan et al., 2013). Thus, both normal and cancer cells express the CD146 molecule. Likewise, microparticles contained in the bloodstream and generated from both endothelial (Dignat-George et al., 2011) and CD146-positive cancer cells (De Souza et al., 2016) exhibit CD146 at their surface.

Up to now, it was impossible to target the CD146 form specifically expressed by cancer cells or derivatives thereof such as circulating cancer cells or microparticles, leading to major problems for diagnosis and/or targeted therapy. Only two neutralizing monoclonal antibodies targeting the membrane form of CD146 have been generated until now. ABX-MA1 decreases tumor growth and vascularization but targets both the tumor and the endothelial membranous CD146 and thus displays negative effects on the host vascularization (Mills et al., 2002). More recently, AA98 mAb has been generated that specifically targets the membranous CD146 expressed by tumor vessels (Lin et al., 2007). However, this antibody does not interact with cancer cells. The M2J-1 mAb, as well as antibodies described in WO 2010/086405, specifically target the soluble form of CD146 but not the tumor form thereof (Stalin et al., 2016). Nodomi et al. ("CD146 is a novel marker for highly tumorigenic cells and a potential therapeutic target in malignant rhaboid tumor", ONCOGENE, vol. 35, no. 40, 4 Apr. 2016, pages 5317-5327) describes CD146 as a potential therapeutic target in malignant rhabdoid tumor and a polyclonal anti-CD146 antibody inhibiting tumor growth of MRT cells. None of the available antibodies is capable of specifically binding a CD146 form which would only be expressed by cancer cells.

In term of diagnosis, it is worth noting that today, tumor cells are detected by imaging with common markers such as $^{18}$FDG which do not permit to distinguish between tumors (Singnurkar et al., 2017). Consequently, there is also a need for new tools capable of discriminating tumors and of allowing a personalized medicine. For instance, in PET imaging, such a tool would be useful for the specific detection of CD146-positive tumors before carrying out any targeted therapy. Hernandez et al. ("ImmunoPET Imaging of CD146 expression in Malignant Brain Tumors", MOLECULAR PHARMACEUTICS, vol. 13, no. 7, 1 Jun. 2016, pages 2563-2570) describes the use of a radiolabeled anti-CD146 antibody YY146 in PET imaging but does not describe an antibody directed specifically against CD146-positive tumors or having an anti-tumor therapeutic effect".

Inventor's hypothesis was that the tumor CD146 molecule (protein) displays structural features different from that of the "physiological" CD146 molecule expressed in the vascular system. Thus, they have generated several antibodies able to recognize the extracellular part of CD146. Then, these antibodies were screened for their ability to recognize CD146 expressed by cancer cells but not CD146 expressed by other types of cell. Inventors now herein describe for the first time an antibody (herein referred to as TsCD146 mAb for Tumor specific anti-CD146 monoclonal antibody) displaying these properties. Such an antibody is of major interest to detect and/or specifically target the tumor form of CD146 (herein designated as "tumor CD146") without affecting CD146 expressed by normal cells and without affecting vascular or immune integrity and functions.

SUMMARY OF THE INVENTION

Inventors herein describe tumor specific anti-CD146 antibodies (i.e. antibodies directed against tumor CD146, i.e. against a CD146 form expressed by tumor cells or associated in any way to tumor cells, and not against a CD146 form which is not expressed by, or associated in any way to, tumor cells) as well as uses thereof for prevention, treatment, diagnosis, prognosis and/or monitoring purposes, in particular for use as an imagery tracer.

Hence, in a first aspect, inventors herein describe an antibody as well as fragments thereof, directed against a CD146 protein, typically a CD146 form expressed by tumor cells or associated in any way to tumor cells, also herein identified as "tumor CD146". A preferred antibody or fragment thereof comprises the light chain variable region (VL) CDR polypeptide sequence of SEQ ID NO: 1, SEQ ID NO: 2 and SEQ ID NO: 3, and the heavy chain variable region (VH) CDR polypeptide sequence of SEQ ID NO 4, SEQ ID NO: 5 and SEQ ID NO: 6.

In another aspect, inventors herein describe a nucleic acid molecule, typically an isolated nucleic acid molecule, encoding an antibody or a fragment thereof as described herein above, a vector comprising such a nucleic acid molecule, and a host cell comprising such a nucleic acid molecule or vector.

Also herein described is a pharmaceutical composition comprising at least one compound selected from the group consisting of an antibody and/or a fragment thereof, a nucleic acid molecule, a vector and/or a host cell as described herein above, and optionally, a pharmaceutically acceptable carrier or support.

In another aspect, the invention relates to any of the herein above described products for use as a medicament, in particular for use for preventing and/or treating cancer in a subject, typically in a patient, preferably a cancer selected from a melanoma, a kidney cancer, a pancreatic cancer and a colon cancer.

Also herein described is an in vitro, in vivo or ex vivo diagnostic and/or prognostic method of cancer in a subject wherein said method comprises a step of determining the CD146 protein expression and/or the level of expression in a biological sample of said subject using said antibody and/or fragment thereof as herein described.

Further herein described is an in vitro, in vivo or ex vivo method for monitoring the response to an anticancer treatment of a subject suffering from cancer comprising determining the CD146 protein level of expression in a biological sample of said subject using at least said one antibody and/or a fragment thereof at two or more time points during said anticancer treatment, wherein an equal or higher CD146 protein level of expression in a biological sample of the subject at a later time point, compared to a reference value obtained in a biological sample of the subject at an earlier time point, is indicative of a resistance of the subject to said anticancer treatment whereas a lower CD146 protein level is indicative of a response, for example of a prolonged response, of the subject to said anticancer treatment.

Inventors also herein describe a kit suitable for carrying out any one of the herein described diagnostic, prognostic and/or monitoring methods, wherein the kit comprises at least a herein described anti-tumor CD146 antibody and/or a fragment thereof, as well as corresponding uses of such a kit.

In another aspect, inventors herein describe an antibody, or of a fragment thereof, wherein said antibody or fragment is labelled with a radioactive element, and optionally conjugated to a chelator, as well as uses of such a labelled antibody or fragment as an imagery tracer, for example as a Single Photon Emission Computed Tomography (SPECT-CT) tracer or as a Positron Emission Tomography-Computed Tomography (PET-CT) tracer.

The present invention also relates to the hybridoma deposited on Apr. 10, 2017 at the Collection Nationale de Cultures de Microorganismes (CNCM) under the number CNCM I-5246.

DETAILED DESCRIPTION OF THE INVENTION

Unless defined otherwise, all technical and scientific terms used herein have the same meaning as commonly understood to one skilled in the relevant art. For convenience, the meaning of certain terms and phrases employed in the specification and claims are provided.

Antibody and Fragment Thereof

The present invention relates to an antibody, typically an isolated antibody, as well as any fragment thereof, which is directed against a CD146 protein, typically a CD146 form expressed by tumor cells or associated in any way to tumor cells, also herein identified as "tumor CD146". Preferably this antibody does not recognize or bind a CD146 form which is not expressed by, or associated in any way to, tumor cells.

In a preferred embodiment, the antibody or fragment thereof according to the invention comprises the light chain variable region (VL) CDR polypeptide sequence of SEQ ID NO: 1, sequence NAN and SEQ ID NO: 2, and the heavy chain variable region (VH) CDR polypeptide sequence of SEQ ID NO 3, SEQ ID NO: 4 and SEQ ID NO: 5.

SEQ ID NO:1 correspond to the following amino acid sequence: QNIYKN

SEQ ID NO:2 correspond to the following amino acid sequence: QQYYSGWT

SEQ ID NO:3 correspond to the following amino acid sequence: SGFTFSNYG

SEQ ID NO:4 correspond to the following amino acid sequence: YISHDGGS

SEQ ID NO:5 correspond to the following amino acid sequence: DTTDYYFDYW

In a particular aspect, the antibody or fragment thereof according to the invention comprises a light chain variable region (VL) comprising SEQ ID NO: 6 and a heavy chain variable region (VH) comprising SEQ ID NO: 7.

Inventors have demonstrated that antibody or fragments thereof according to the invention have the ability to recognize CD146 expressed by cancer cells (also herein identified as "tumor CD146") but not CD146 expressed by other cell types (also herein identified as "physiological CD146"); (see experimental part). This means that the antibody or fragment thereof of the invention is capable of specifically recognizing the tumor form of CD146 and not the physiological form thereof. This also means that the antibody or fragment thereof of the invention recognizes CD146-positive tumors and are capable of distinguishing them from healthy tissues.

The term "antibody" as used herein is intended to designate a monoclonal antibody, as well as a multispecific antibody (i.e. an antibody comprising a first antigen binding site and at least one second different antigen binding site; e.g. a bispecific antibody).

More particularly, an antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as VH) and a heavy chain constant region (hereafter CH). Heavy chains are classified as gamma, mu, alpha, delta, or epsilon, and define the antibody's isotype as IgG, IgM, IgA, IgD, and IgE, respectively. The heavy chain constant region of the immunoglobulin IgG, IgD, and IgA (γ, δ and α chains respectively) comprises three domains (CH1, CH2, and CH3) and a hinge region for added flexibility, and the heavy chain constant region of the immunoglobulin IgM and IgE contains 4 domains (CH1, CH2, CH3, and CH4).

The antibody of the invention can be of the IgG, IgM, IgA, IgD, and IgE isotype, depending on the structure of its heavy chain. However, in a preferred embodiment, the antibody of the invention is of the IgG isotype, i.e., its heavy chain is of the gamma (γ) type.

IgG antibodies are classified in four distinct subtypes, namely IgG1, IgG2, IgG3 and IgG4 in the order of their abundance in serum (IgG1 being the most abundant). The structure of the hinge regions in the γ chain gives each of these subtypes its unique biological profile (even though there is about 95% similarity between their Fc regions, the structure of the hinge regions is relatively different).

The antibody of the invention can be of the IgG1, IgG2, IgG3 or IgG4 subtype. However, in a preferred embodiment, the antibody of the invention is of the IgG1 subtype.

Each light chain comprises a light chain variable region (abbreviated herein as VL) and a light chain constant region comprising only one domain, CL. There are two types of light chain in mammals: the kappa (κ) chain, encoded by the immunoglobulin kappa locus on chromosome 2, and the lambda (λ) chain, encoded by the immunoglobulin lambda locus on chromosome 22. In a preferred embodiment, the antibody of the invention has a Kappa light chain.

The VH and VL regions can be further subdivided into regions of hypervariability, termed "Complementarity Determining Regions" (CDR), which are primarily responsible for binding an epitope of an antigen, and which are interspersed with regions that are more conserved, termed "Framework Regions" (FR). Each VH and VL is composed of three CDRs and four FRs, arranged from amino-terminus to carboxy-terminus in the following order: FR1, CDR1, FR2, CDR2, FR3, CDR3, FR4. The functional ability of the antibody to bind a particular antigen depends on the variable regions of each light/heavy chain pair, and is largely determined by the CDRs.

The variable region of the heavy chain differs in antibodies produced by different B cells, but is the same for all antibodies produced by a single B cell or B cell clone (or hybridome).

By contrast, the constant regions of the antibodies mediate the binding of the immunoglobulin to host tissues or factors, including various cells of the immune system (e.g. effector cells) and the first component (Clq) of the classical complement system.

As used herein, the term "antibody fragments" intends to designate Fab, Fab', F(ab')2, scFv, dsFv, ds-scFv, dimers, minibodies, diabodies, and multimers thereof and bispecific antibody fragments. Antibodies can be fragmented using conventional techniques. Various techniques have been developed for the production of antibody fragments. Traditionally, these fragments were derived via proteolytic digestion of intact antibodies. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Preferably the antibody fragment of the invention is a F(ab')2 fragment.

Typically, the antibody fragment of the invention is a functional fragment, i.e. an antibody fragment capable of binding and preferably inhibiting or neutralizing the activity of a CD146 molecule as does the antibody it is deriving from, typically capable of binding a "tumor CD146", i.e. a CD146 form expressed by tumor cells or associated in any way to tumor cells, and not capable of binding a 'non-tumoral CD146", i.e. a CD146 form which is not expressed by tumor cells or which is not associated in any way to tumor cells.

In another particular embodiment, the antibody of the invention is a monoclonal antibody.

A "monoclonal antibody", as used herein, designates an antibody arising from a nearly homogeneous population of antibodies. More particularly, the antibodies of a given subject are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one isotype and subtype, and light chains of only one type. In addition, in contrast with preparations of polyclonal antibodies, each monoclonal antibody is directed to a single epitope of an antigen.

To produce monoclonal antibodies, antibody producing cells (lymphocytes) can be harvested from an immunized animal as described above and fused with myeloma cells by standard somatic cell fusion procedures thereby immortalizing these cells and yielding hybridoma cells. Such techniques are well known in the art (e.g. the hybridoma technique originally developed by Kohler and Milstein (1975)) as well as other techniques such as the human B-cell hybridoma technique, the EBV-hybridoma technique to produce human monoclonal antibodies, and screening of combinatorial antibody libraries. Hybridoma cells can be screened immunochemically for production of antibodies specifically reactive with the target polypeptide(s) so that only monoclonal antibodies binding to said polypeptide(s) are isolated.

The antibody or a fragment thereof of the invention may be a human, chimeric, humanized, murine, CDR-grafted, phage-displayed, bacteria-displayed, yeast-displayed, transgenic-mouse produced, mutagenized, or randomized antibody or fragment.

A chimeric antibody is a molecule in which different portions are derived from different animal species, such as those having a variable region derived from a murine monoclonal antibody (mAb) and a human immunoglobulin constant region.

Humanized forms of antibodies of the invention are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin (recipient antibody) are replaced by corresponding non-human residues of the donor antibody. Furthermore, humanized antibodies may comprise residues that are not found in the recipient antibody or in the donor antibody. In general, the humanized antibody may comprise substantially all of at least one, typically two, variable domains, in which all or substantially all of the hypervariable loops correspond to those of a non-human immunoglobulin (donor antibody having the desired specificity, affinity, and capacity) and all or substantially all of the FRs are those of a human immunoglobulin sequence. Methods for humanizing non-human antibodies have been described in the art. Preferably, a humanized antibody has one or more amino acid residues introduced into it from a source, which is non-human. These non-human amino acid residues are often referred to as "import" residues, which are typically taken from an "import" variable domain. Humanization may be essentially performed by substituting hypervariable region sequences for the corresponding sequences of a human antibody. Accordingly, such humanized antibodies are chimeric wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. Other methods generally involve conferring donor CDR binding affinity onto an antibody acceptor variable region framework. One method involves simultaneously grafting and optimizing the binding affinity of a variable region binding fragment. Another method relates to optimizing the binding affinity of an antibody variable region.

The antibody or fragment thereof of the invention may be administered in their "naked" or unconjugated form, or may have other agents conjugated to them, such as drug, toxin or radioactive atom.

Examples of toxins that can be conjugated to said antibody or fragment thereof are Monomethyl auristatin E, an auristatin (MMAE) or a derivative thereof, or Cholera toxin.

In a particular embodiment, the antibody or fragment thereof of the invention, which is directed against the tumor CD146 protein, comprises or consists of the light chain variable region (VL) of sequence SEQ ID NO: 6 and the heavy chain variable region (VH) of sequence SEQ ID NO: 7.

SEQ ID NO: 6 consists of the following amino acid sequence:

DIQMTQSPSLLSASVGDRVTLNCKASQNIYKNLAWYQQKLGEAPKLLIYN

ANSLQTGIPSRFSGSGSGTELTLTISSLQPEDVATYFCQQYYSGWTFGGG

TKLELK

SEQ ID NO: 7 consists of the following amino acid sequence:

EEQLVESGGGLVQPGRSMKLSCAASGFTFSNYGMAWVRQAPKKGLEWVAY

ISHDGGSTYYRDSVKGRFTISRDNAKSTLYLQMDSLRSEDTATYYCTTDT

TDYYFDYWGQGVMVTVSS

A preferred antibody of the invention is the monoclonal antibody produced by the hybridoma deposited on Apr. 10, 2017 at the Collection Nationale de Cultures de Microorganismes (CNCM) under number CNCM I-5246.

It shall be understood that the invention also relates to an antibody or fragment thereof which can compete with the monoclonal antibody deposited on Apr. 10, 2017 at the CNCM under number CNCM I-5246. The address of CNCM is: INSTITUT PASTEUR, 25 RUE DU DOCTEUR ROUX, 75724 PARIS CEDEX 15-5246. As used herein, the term "antibody fragments" intends to mean that said antibody or fragment thereof essentially binds to the same epitope as the monoclonal antibody produced by the hybridoma deposited at the CNCM under number CNCM I-5246.

Hybridoma

The present invention also relates to the hybridoma deposited on Apr. 10, 2017 at the Collection Nationale de Cultures de Microorganismes (CNCM) under the number CNCM I-5246. Such Hybridoma has been obtained by immunisation of rat with a recombinant protein generated in mouse myeloma, corresponding to the extracellular part of CD146. Such an extracellular part of CD146 typically comprises or consists of an amino acid sequence comprising or consisting of a sequence selected from SEQ ID NO: 8, SEQ ID NO: 9, SEQ ID NO: 10, SEQ ID NO: 11, SEQ ID NO: 12, SEQ ID NO: 13, and SEQ ID NO: 14, preferably SEQ ID NO: 14.

Nucleic Acid Encoding and Antibody or Fragment Thereof

The invention also relates to a nucleic acid molecule, in particular to an isolated nucleic acid molecule, encoding an antibody or a fragment thereof according the invention.

The term "nucleic acid molecule" refers to a polymeric form of nucleotides, either deoxyribonucleotides (DNA sequence) or ribonucleotides (RNA sequence), or any analog thereof Vector Comprising a Nucleic Acid Also herein described is a vector comprising a nucleic acid molecule according to the invention, typically a nucleic acid encoding an antibody or a fragment thereof according to the invention. The vector can be a vector appropriate for semi-stable or stable expression. In particular, the vector according to the invention is a cloning vector or an expression vector. The vector can be a viral vector such as a bacteriophage or a non-viral vector such as a plasmid.

Host Cell Comprising a Nucleic Acid or a Vector

The present disclosure also relates to a host cell comprising a nucleic acid molecule according to the invention, typically a nucleic acid encoding an antibody or a fragment thereof according to the invention, or a vector comprising or encoding such a nucleic acid molecule.

Pharmaceutical Composition

The invention also relates to a pharmaceutical composition comprising at least one product as herein described, typically a product selected from the group consisting of:
  an antibody and/or a fragment thereof according to the invention, a nucleic acid molecule encoding an antibody and/or a fragment thereof according to the invention;

a vector comprising or encoding a nucleic acid molecule according to the invention; and a host cell comprising a nucleic acid and/or a vector according to the invention.

The advantageous embodiments are as defined above.

The pharmaceutical composition typically comprises an antibody or a fragment thereof according to the invention, optionally together with a pharmaceutically acceptable carrier or support.

Such a product is typically present in the pharmaceutical composition or medicament according to the invention in a therapeutically effective amount (i.e. in an active and non-toxic amount). A therapeutically effective amount refers to that amount of compound which ameliorates the symptoms or condition. Therapeutic efficacy and toxicity may be determined by standard pharmaceutical procedures in cell cultures or experimental animals, e.g., ED50 (the amount therapeutically effective in 50% of the population) and LD50 (the dose lethal to 50% of the population). The amount ratio of toxic to therapeutic effects is the therapeutic index and can be expressed as the ratio, LD50/ED50. Pharmaceutical compositions which exhibit large therapeutic indices are preferred.

For example, the antibody according to the invention, can be administered to a patient, in particular intravenously, in an amount, within the range from 0.1 µg/kg to 100 mg/kg, particularly from 1 mg/kg to 50 mg/kg of body weight of said patient at least every month, particularly at least every three weeks, more particularly at least every two weeks and even more particularly at least every week.

The pharmaceutical composition according to the invention may be administered by a variety of routes including, but not limited to, oral, intravenous, intramuscular, intraarterial, intramedullary, intrathecal, intraventricular, transdermal, subcutaneous, intraperitoneal, intranasal, enteral, topical, sublingual, rectal or ocular route.

As indicated previously, in addition to the active ingredients, the pharmaceutical composition of the invention may contain a suitable pharmaceutically acceptable carrier or support comprising an excipient or auxiliary, which facilitates processing of the active compounds into preparations which can be used pharmaceutically. In a particular aspect, the pharmaceutical composition according to the invention is formulated in a pharmaceutical acceptable carrier. Pharmaceutical acceptable carriers are well known by one skilled in the art. For example, the pharmaceutical acceptable carrier comprises or is an isotonic solution.

Use as a Medicament

Herein described are also an antibody or a fragment thereof according to the invention, a nucleic acid encoding such an antibody or fragment thereof, a vector, a host cell, and a pharmaceutical composition as herein described for use as a medicament.

Use for Preventing or Treating Cancer

The invention also relates to an antibody according to the invention, a fragment thereof, a nucleic acid molecule, a vector, a host cell and/or a pharmaceutical composition as herein described for use for preventing or treating cancer in a subject, typically a cancer in which CD146 is expressed, in particular a cancer wherein cancer cells express CD146 at high level, preferably a cancer selected from melanoma, prostatic cancer, breast cancer, lung cancer, pancreatic cancer, kidney cancer, gastric cancer, hepatic cancer, colon cancer, and more preferably a cancer selected from melanoma, pancreatic cancer, kidney cancer and colon cancer.

Indeed, inventors demonstrated and herein reveals that the herein described antibodies and fragments thereof according to the invention, have the properties of recognizing CD146 expressed by cancer cells ("tumor CD146") but not CD146 expressed by distinct cell types ("physiological CD146"), and are capable of decreasing cancer cells proliferation in vitro and in vivo, whereas it has no side effect on non-tumor cells (see experimental part).

The invention also relates to the use of at least one compound selected from the group consisting of:

an antibody and/or a fragment thereof according to the invention, a nucleic acid molecule encoding an antibody and/or a fragment thereof according to the invention;

a vector comprising or encoding a nucleic acid molecule according to the invention; and a host cell comprising a nucleic acid and/or a vector according to the invention, for the preparation of a medicament for preventing or treating cancer, in particular a cancer selected from melanoma, prostatic cancer, breast cancer, lung cancer, pancreatic cancer, kidney cancer, gastric cancer, hepatic cancer and colon cancer, more preferably a cancer selected from melanoma, pancreatic cancer, kidney cancer and colon cancer.

The invention also relates to a method for the prophylaxis (prevention) or treatment of cancer, preferably of a cancer selected from melanoma, prostatic cancer, breast cancer, lung cancer, pancreatic cancer, kidney cancer, gastric cancer, hepatic cancer and colon cancer, more preferably of a cancer selected from melanoma, pancreatic cancer, kidney cancer and colon cancer, in a subject in need thereof, said method comprising a step of administering to the subject a therapeutically or prophylactically effective amount of at least one product selected from the group consisting of:

an antibody and/or a fragment thereof according to the invention, a nucleic acid molecule encoding an antibody and/or a fragment thereof according to the invention;

a vector comprising or encoding a nucleic acid molecule according to the invention; and a host cell comprising a nucleic acid and/or a vector according to the invention.

The therapeutic method according to the invention can further comprise a step of administering a therapeutically or prophylactically effective amount of at least one additional distinct compound of interest (e.g. an anti-tumor agent, an anti-angiogenic compound, or an anti-inflammatory compound) to the subject in need thereof.

The term "subject" or "patient" as used herein refers to an animal, typically a mammal. The mammal may be a primate, particularly a human being; a domestic mammal such as horse, cattle, and sheep; a companion animal such as a dog or a cat, or a zoo mammal such as a felid, canid, bovid or ungulate. In a preferred embodiment, the mammal is a human being, whatever its age or sex. Unless otherwise specified in the present disclosure, the subject has a tumor or cancer, typically a melanoma, pancreatic cancer or colon cancer.

As used herein, the terms "anti-tumor agent" refer to any compound that prevents tumor growth or promotes tumor shrinking. An appropriate anti-tumor agent can be selected from an anti-angiogenic compound, a DNA intercalator/ Cross-linker (like oxaliplatin or mitoxantrone for example), a DNA Synthesis Inhibitor (like cytosine β-D-arabinofuranoside or 5-Fluorouracil for example), a DNA-RNA Transcription Regulator (such as doxorubicin or actinomycin D for example) and a Microtubule Inhibitor (such as paclitaxel or nocodazole for example).

As used herein, the term "anti-angiogenic compound" refers to any compound that inhibits the development of a pathological vascular network, typically the vascular network of a tumor, in particular of a malignant tumor.

In particular, the anti-angiogenic compound is selected from the group consisting of:
- an anti-VEGF antibody, like bevacizumab (particularly for the treatment and/or prevention of cancer) or ranibizumab (particularly for the treatment and/or prevention of age-related macular degeneration);
- an anti-soluble CD146 antibody as described in WO2010/086405;
- an anti-EGF receptor antibody, like cetuximab;
- an inhibitor of a receptor involved in angiogenesis including VEGFR1, VEGFR2, VEGFR3, CSFR or PDGFR, like sunitinib, sorafenib, axitinib or regorafenib;
- an inhibitors of m-TOR, like everolimus or temsirolimus; and
- an inhibitor of an EGF receptor, like erlotinib.

As used herein, the term "anti-inflammatory compound" refers to any compound that reduces inflammation. In particular, anti-inflammatory compound can be corticoid and nonsteroid anti-inflammatory agent ibuprofen derivative.

Said antibody or fragment thereof, said nucleic acid molecule, said vector and/or said host cell according to the invention, optionally together with an additional distinct compound of interest, can be administrated simultaneously, separately or sequentially.

Use for Detection, Diagnosis or Prognosis

The invention also relates to a method for detecting the CD146 protein, in particular the "tumor CD146 protein" in a sample, typically in a biological sample. This method comprises a step of incubating the sample with an antibody or a fragment thereof according to the invention.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor cells or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components. Preferably, the biological sample is a biopsy, in particular a tumor biopsy.

In particular, the method according to the invention for detecting a CD146 protein, more particularly a "tumor CD146 protein" in a sample, further comprises a step of detecting the binding of an antibody according to the invention with a CD146 protein, typically with a "tumor CD146 protein".

The method according to the invention for detecting a CD146 protein, in particular a "tumor CD146 protein" in a sample can be based on various techniques, well known by one skilled in the art, including, but not limited to:
- a western blot assay (the CD146 protein, in particular the "tumor CD146 protein", in a cell lysate or in a solution being immobilized on a membrane, said membrane being thereafter incubated with an antibody of the invention or a fragment thereof, preferably a labeled antibody or fragment thereof, in appropriate conditions well-known in the art),
- an ELISA assay (the CD146 protein, in particular the "tumor" CD146 protein" being immobilized on a microtiter plate, said plate being thereafter incubated with an antibody or a fragment thereof of the invention, preferably a labeled antibody or fragment thereof, in appropriate conditions well-known in the art),
- an immunohistochemistry assay (the antibody or fragment thereof according to the invention, preferably a labeled antibody or fragment thereof, being used to stain a sample containing fixed cells or tissues expressing a CD146 protein, in particular suspected of containing a "tumor CD146 protein"),
- a flow cytometry assay (the antibody or fragment thereof according to the invention, preferably a labeled antibody or fragment thereof, being used to stain a sample containing fixed or living cells expressing a CD146 protein, in particular suspected of containing a "tumor CD146 protein", in appropriate conditions well-known in the art).

In one embodiment of the method for detecting the CD146 protein, in particular the "tumor CD146 protein" in a sample, the antibody or fragment thereof of the invention is coated on a solid support.

Any other detection techniques requiring the use of an antibody are herein encompassed. The presence and optionally the amount of said CD146 protein, in particular "tumor CD146 protein", in the sample can be determined thanks to these techniques. Some of these techniques require labeling the antibody of the invention with a detectable marker, preferably a fluorescent or a luminescent marker, as disclosed herein above.

The invention also relates to a method for purifying a CD146 protein, in particular a "tumor CD146 protein" from a sample, comprising the step of incubating said sample with the antibody or fragment thereof according to the invention.

The method for purifying a CD146 protein, in particular a "tumor CD146 protein" from a sample, can be based on various techniques, well known by one skilled in the art, including, but not limited to flow cytometry assays and immunoprecipitation assays.

Also herein described is a kit useful/suitable for carrying any one of the herein described methods for detecting a CD146 protein, in particular a "tumor CD146 protein" in a sample, and/or for purifying a CD146 protein, in particular a "tumor CD146 protein" according to the invention from a sample; said kit comprising:
- at least one antibody and/or fragment thereof according to the invention; and
- at least one reagent for detecting said antibody and/or fragment thereof according to the invention.

The reagent for detecting an antibody according to the invention can be selected from the group consisting of an ELISA reagent, a Western blot reagent, and a dot blot reagent.

The present disclosure also relates to an in vitro, in vivo or ex vivo diagnostic and/or prognostic method of cancer in a subject wherein the method comprises a step of determining the CD146 protein, in particular "tumor CD146 protein", expression and/or level of expression, in a biological sample of the subject using at least one antibody and/or fragment thereof according to the invention.

The cancer is typically a cancer in which cancer cells express CD146, in particular express CD146 at high level. Preferably the cancer is selected from melanoma, prostatic cancer, breast cancer, lung cancer, pancreatic cancer, kidney cancer, gastric cancer, hepatic cancer and colon cancer, more preferably a cancer selected from melanoma, pancreatic cancer, kidney cancer and colon cancer.

In fact, inventors demonstrated and herein reveal that the antibodies and fragment thereof according to the invention, which recognize the CD146 form expressed by cancer cells (herein identified as "tumor CD146") but not CD146 expressed by other types of cell ("physiological CD146"), allow the detection of tumor cells without affecting vascular or immune integrity and functions. Using said antibodies or any fragment thereof according to the invention confers a better specificity to the herein described methods. It is also helpful for the specific detection of CD146-positive tumors before carrying out any targeted therapy.

The term "determination" or "determining" as used herein may refer to identification (qualitative determination) and/or to quantification (quantitative determination).

The term "expression" refers to the process by which a polynucleotide sequence undergoes successful transcription and translation such that detectable proteins are expressed.

Any variety of know methods may be used for detecting the CD146 protein, typically the "tumor CD146 protein", in a biological sample of a subject by using the antibody or fragment thereof of the invention such as immunoassay, immunosorbent assay (ELISA), radioimmunoassay (RIA), and the like.

For example, when the biological sample is a biopsy, the method can be performed by using a primary antibody or a fragment thereof according to the invention and a secondary antibody directed to said primary antibody or fragment thereof, said secondary antibody being coupled to a fluorochrome, such as Alexa Fluor 488 for example. In such an example, the expression of the CD146 protein, typically of the "tumor CD146 protein" is determined qualitatively.

In another example, the method can be performed via an ELISA assay, wherein the antibody or fragment thereof of the invention is immobilized on a microtiter plate, said plate being thereafter incubated with at least one labelled secondary antibody directed to a CD146 protein in appropriate conditions well-known in the art. Said labeled secondary antibody can be for example the S-Endo1 antibody (clone number F4-35H7) commercialized by Biocytex company which is directed to CD146 protein (but not specific of the tumor form of CD146). On the contrary, the S-endo1 antibody can be immobilized on a microtiter plate and the antibody or fragment thereof of the invention can be used as the labelled secondary antibody.

Advantageously, the antibody or fragment thereof according to the invention is capable of detecting circulating cancer cells and/or microparticles that are released by tumors, which allows said method to be performed by a minimally invasive technique. Thus, in embodiment particular aspect, the biological sample is a liquid biopsy (i.e. a non-solid biological tissue) such as blood or plasma.

The term "microparticles" (MPs) as used herein refers to heterogeneous plasma membranes vesicles (0.1-1 μm) bearing proteins and biomarkers of their cells of origin. MPs are released from different cell types, such as platelets, endothelial cells, leukocytes, and erythrocytes, via the budding of the outer cell membrane during cell activation or apoptosis.

Preferably, when the method comprises the determination of the level of expression of the CD146 protein, said in vitro diagnostic and/or prognostic method can comprise an additional step of comparing the CD146 protein level of expression to a reference value (i.e. to a threshold or control level) thereby determining if said subject is affected with a cancer or has a poor prognosis. Preferably, in said additional step, it is determined if the level of expression is significantly higher than the reference value; said significantly higher level of expression indicating that the subject is affected with a cancer, typically a melanoma, kidney cancer, pancreatic cancer or colon cancer or has a poor prognosis. The reference value is typically the expression level of the CD146 protein, in particular of the "tumor CD146 protein", in a biological sample from a healthy subject or from a subject who is not affected with a cancer.

The "reference value" may vary depending on the type of tested biological sample and on the method used for determining the level of expression of the CD146 protein, typically of the "tumor CD146 protein". A suitable "reference value" includes the expression level of the CD146 protein, typically of the "tumor CD146 protein", determined in the same type of biological sample from a healthy subject or from a subject who is not affected with a cancer or tumor. Preferably, the "reference value" is the mean expression levels of the CD146 protein, typically of the "tumor CD146 protein" determined in the same type of biological sample of several healthy subjects or several subjects who are not affected with a cancer or tumor. The "reference value" may also be the value as determined in a biological sample which has been taken earlier from the same subject.

The significant higher level of expression of the CD146 protein, typically of the "tumor CD146 protein", can correspond to an increase of expression of at least more than 10%, more than 15%, more than 20% more than 25% or more than 30% when compared to the referenced value.

The term "subject" is to be interpreted as previously indicated herein above.

Use for Monitoring

The invention also relates to an in vitro, in vivo or ex vivo method for monitoring the response to an anticancer treatment of a subject suffering from cancer comprising: determining the CD146 protein level of expression in a biological sample of said subject using at least one antibody and/or a fragment thereof as defined in any one of claims 1 to 4 at two or more time points during said anticancer treatment, wherein an equal or higher CD146 protein level of expression in a biological sample of the subject at a later time point, compared to a reference value obtained in a biological sample of the subject at an earlier time point, is indicative of a resistance of the subject to said anticancer treatment whereas a lower CD146 protein level of is indicative of a response, typically of a prolonged response, of the subject to said anticancer treatment.

Again, and as indicated previously, the cancer is typically a cancer in which cancer cells express CD146, in particular in which cancer cells express CD146 at a high level. Preferably the cancer is cancer is selected from melanoma, prostatic cancer, breast cancer, lung cancer, pancreatic cancer, kidney cancer, gastric cancer, hepatic cancer and colon cancer, more preferably a cancer selected from melanoma, pancreatic cancer, kidney cancer or colon cancer. The term "subject" is also to be interpreted as previously indicated herein above.

Kit Suitable for Diagnosis, Prognostic or Monitoring and Uses Thereof

The invention also relates to a kit suitable for carrying out any herein described methods of the invention, typically (i) a diagnostic and/or prognostic method of a cancer in a subject or (ii) a monitoring method of the response of a subject to an anticancer treatment, said kit comprising at least one antibody or fragment thereof according to the invention.

The kit typically provides additional components that are useful for carrying out the methods of the invention including, but not limited to a component selected from at least one buffer, reagent, label, reacting surface, means for detection, control sample, standard, and note of instructions. Preferably, the kit comprises at least one reagent for detecting and/or visualizing the antibody or fragment thereof according to the invention.

The invention also relates to the use of a kit for carrying out typically (i) the herein described diagnostic and/or prognostic method of a cancer in a subject or (ii) the monitoring method of the response to an anticancer treatment of a subject, said kit comprising at least one antibody or fragment thereof according to the invention and, optionally and preferably, at least one reagent for detecting and/or visualizing said antibody or fragment thereof according to the invention.

Antibody or Fragment Thereof Labelled with a Radioactive Element

The invention also relates to an antibody or a fragment thereof of the invention as herein described (typically a TsCD146 mAb or a fragment thereof) labelled with a radioactive element. A preferred radioactive element is Gallium 68.

Preferably, the antibody or fragment thereof is conjugated to a chelator. Such a chelator is preferably 1,4,7-triazacyclononane,1-glutaric acid-4,7 acetic acid (NODAGA).

In a particular embodiment, the antibody's fragment is a F(ab')2 fragment, typically the TsCD146 F(ab')2, and said fragment is conjugated to 1,4,7-triazacyclononane,1-glutaric acid-4,7 acetic acid (NODAGA) and labelled with Gallium 68 ($Ga^{68}$). The TsCD146 F(ab')2 fragment which is to be conjugated to NODAGA and labelled with Gallium 68 comprises a light chain variable region (VL) comprising or consisting of SEQ ID NO: 6 and a heavy chain variable region (VH) comprising or consisting of SEQ ID NO: 7.

Use as an Imagery Tracer

The invention also relates to the use of an antibody or of a fragment thereof according to the invention as an imagery tracer, typically as Single Photon Emission Computed Tomography (SPECT-CT) tracer or as a Positron Emission Tomography-Computed Tomography (PET-CT) tracer, said antibody or fragment thereof being labelled with a radioactive element.

It is reminded that positron emission tomography ("PET" or "PET scan") or Positron Emission Tomography-Computed Tomography (PET-CT) is a nuclear medicine, functional imaging technique that is used to observe molecular or metabolic processes in the body. PET is based on the general principle of scintigraphy which consists of introducing into the body a tracer whose behavior and biological properties are known to obtain an image of the functioning of an organ or of the presence of a molecular target. This tracer is typically introduced into the body on a biologically active molecule and is marked by a radioactive element which emits positrons whose annihilation produces two photons. It is the detection in coincidence of these photons that allows the location of the place of their emission and therefore the concentration of the tracer at each point of the targeted tissue, typically of the organ. Three-dimensional images showing in color the zones of high concentration of the tracer within the body are then constructed by computer analysis. In modern PET-CT scanners, three dimensional imaging is often accomplished with the aid of a CT X-ray scan performed on the patient during the same session, in the same machine.

Thus, PET makes it possible to visualize the activities of the cell metabolism: functional imaging as opposed to so-called structural imaging techniques such as those based on X-rays (radiology or CT-scanner) that produce images of anatomy. Therefore, positron emission tomography (PET) is a diagnostic tool that detects certain pathologies that result in an alteration of normal physiology such as cancer.

Single-photon emission computed tomography ("SPECT" or "SPECT-CT", or less commonly, "SPET" or "SPET-CT") is a nuclear medicine tomographic imaging technique using gamma rays. It is very similar to conventional nuclear medicine planar imaging using a gamma camera. However, it is able to provide true 3D information. This information is typically presented as cross-sectional slices through the patient, but can be freely reformatted or manipulated as required. The technique requires delivery of a gamma-emitting radioisotope (a radionuclide) into the patient, normally through injection into the bloodstream. On occasion, the radioisotope is a simple soluble dissolved ion, such as an isotope of gallium (III). Most of the time, though, a radioisotope marker is attached to a specific ligand to create a radioligand able to bind to certain types of tissues. This marriage allows the combination of ligand and radiopharmaceutical to be carried and bound to a place of interest in the body, where the ligand concentration is seen by a gamma camera.

SPECT is similar to PET in its use of radioactive tracer material and detection of gamma rays. In contrast with PET, however, the tracers used in SPECT emit gamma radiation that is measured directly, whereas PET tracers emit positrons that annihilate with electrons up to a few millimeters away, causing two gamma photons to be emitted in opposite directions. A PET scanner detects these emissions "coincident" in time, which provides more radiation event localization information and, thus, higher spatial resolution images than SPECT (which has about 1 cm resolution). SPECT scans, however, are significantly less expensive than PET scans, in part because they are able to use longer-lived more easily obtained radioisotopes than PET.

Nuclear medicine is a medical specialty involving in particular the application of radioactive substances in the diagnosis and treatment of diseases. Nuclear medicine, in a sense, is "radiology done inside out" or "endoradiology" because it records radiation emitting from within the body rather than radiation that is generated by external sources like X-rays. Single Photon Emission Computed Tomography or SPECT and Positron Emission Tomography or PET scans are the two most common imaging modalities in nuclear medicine. The use of imaging and corresponding companion tools to detect tumor is of crucial interest in the management of patients, not only for diagnosis but also for implementing targeted therapy.

In this context, inventors showed that the antibody or fragment thereof of the invention can be labeled with a radioactive element, typically a pharmaceutically acceptable radioactive element, in order to be used as an imagery tracer, typically as SPECT-CT tracer or PET-CT tracer for detecting in particular in vivo CD146-positive tumors. They have been able to produce in particular a $Ga^{68}$-NODAGA-F(ab')2 tracer that can be used in vivo for imaging (see experimental part).

In a preferred embodiment, the radiolabeled antibody or fragment thereof of the invention is in addition conjugated to a chelator. The chelator forming a conjugate compound with the antibody or fragment thereof of the invention is typically selected from 1,4,7-triazacyclononane,1-glutaric acid-4,7 acetic acid (NODAGA), 1,4,7,10-tetraazacyclododecane-1,4,7,10-tetraacetic acid (DOTA), 1,4,7-triazacyclononane-triacetic acid (NOTA), N,N'-Bis(2-hydroxybenzyl)-1-(4-bromoacetamidobenzyl)-1,2-ethylenediamine-N,N'-diacetic acid (HBED), N1-hydroxy-N1-(5-(4-(hydroxy(5-(3-(4-isothiocyanatophenyl)thioureido)pentyl)amino)-4-oxobutanamido)pentyl)-N4-(5-(N-hydroxyacetamido)pentyl)succinamide (DFO), diethylenetriaminepentaacetic acid (DTPA). However, in a preferred aspect, the chelator is NODAGA.

In a typical aspect of the invention, the radioactive element is a pharmaceutically acceptable radioactive element, i.e. a radionuclide adapted for use in medical imagery, preferably for use in PET and/or SPECT imagery, and/or for use in nuclear medicine therapy, typically radiotherapy.

The radioactive elements or radionuclides for use in medical imagery is typically a radioactive element having a short half-live (from about 1 min to 1, 2, 3 or 4 days) such as fluorine 18 (about 110 min), gallium 68 (about 67 min), indium 111 (67 h) and copper 64 (12.7 h). Photon- and low energy (inferior to 300 keV) gamma-emitting radionuclides are preferably used in the context of medical imagery.

The radioactive element can be a radionuclide typically selected from Gallium 68 ($Ga^{68}$), Lutetium 177 ($Lu^{177}$), Fluor 18 ($F^{18}$), Yttrium 90 ($Y^{90}$), Bismuth 213 ($Bi^{213}$), Actinium 225 ($Ac^{225}$), Lead 212 ($Pb^{212}$), Indium 111 ($In^{111}$) and copper 64 ($Cu^{64}$). However, in a preferred aspect, the radioactive element is Gallium 68 ($Ga^{68}$).

The antibody or fragment thereof is as previously defined. However, preferably the antibody or fragment thereof is an antibody fragment and more preferably a F(ab')2 fragment, typically a F(ab')2 fragment comprising a light chain variable region (VL) comprising or consisting of SEQ ID NO: 6 and a heavy chain variable region (VH) comprising or consisting of SEQ ID NO: 7.

When present, the chelator may be linked directly to the antibody or fragment thereof of the invention or through a linker or spacer, the linker or spacer being easily selectable by the person skilled in the art. The linker or spacer is typically covalently coupled to both the chelator and the antibody or fragment thereof of the invention.

The coupling between the antibody or fragment thereof of the invention and the selected radioactive element can be carried out using any chemical, biological or genetic technique known to those skilled in the art. The coupling typically involves one or more covalent, ionic, hydrogen, hydrophobic or Van der Waals bonds, preferably covalent and/or ionic bonds, and can occur at any site of said antibody or fragment thereof amino acid sequence having an adapted functional group such as —OH, —SH, —CO$_2$H, —NH$_2$, —SO$_3$H, —CN, —N$_3$, —NCS, —PO$_2$H, maleimide or succinimide ester, the functional group being naturally present or exogenously (i.e. artificially) introduced.

The radioactive element can be coupled directly to said antibody or fragment thereof (synthesis in tandem) or indirectly via a linker or spacer. In a preferred embodiment, the radioactive element is linked to the antibody or fragment thereof thanks to a chelating agent such as one of those herein above described.

Are in particular herein described $Ga^{68}$-NODAGA-TsCD146 mAb, $Ga^{68}$-DOTA-TsCD146 mAb, $Ga^{68}$-NOTA-TsCD146 mAb, $Ga^{68}$-HBED-TsCD146 mAb, $Ga^{68}$-DFO-TsCD146 mAb, $F^{18}$-NOTA-TsCD146 mAb, $F^{18}$-NODA-TsCD146 mAb, $In^{111}$-DTPA-TsCD146 mAb and $Cu^{64}$-DOTA-TsCD146 mAb. As previously described, "TsCD146 mAb" stands for "Tumor specific anti-CD146 monoclonal antibody".

Are also in particular herein described $Ga^{68}$-NODAGA-TsCD146 F(ab')2, $Ga^{68}$-DOTA-TsCD146 F(ab')2, $Ga^{68}$-NOTA-TsCD146 F(ab')2, $Ga^{68}$-HBED-sCD146 F(ab')2, $Ga^{68}$-DFO-TsCD146 F(ab')2, $F^{18}$-NOTA-TsCD146 F(ab')2, $F^{18}$-NODA-TsCD146 F(ab')2, $In^{111}$-DTPA-TsCD146 F(ab')2 and $Cu^{64}$-DOTA-TsCD146 F(ab')2.

In a typical aspect, inventors herein describe the use of a radiolabeled antibody or fragment thereof of the invention, typically a conjugated and radiolabeled antibody or fragment thereof of the invention, for, or in a method of, labelling, detecting, imaging, measuring, diagnosing, staging and/or monitoring cancer in a subject. The method typically comprises i) administering to the subject a radiolabeled antibody or a fragment thereof of the invention as herein described, ii) performing an imaging method, and iii) determining or analyzing the presence and/or amount of said radiolabeled antibody or fragment thereof. The presence of a signal is typically indicative of the presence of tumor CD146 protein (over) expressing tissue, typically of a cancerous tissue, and/or indicate the stage of disease or disorder as herein described, typically cancer.

The term "analyzing" refers to any method which allows determining if a signal corresponds to a normal signal or not. The analyses may not only be visual but can also involve quantitative analyses. The analyses may include steps of comparing the value of a signal obtained by imagery to the value of the signal of a known healthy tissue of the same subject or of another (reference) subject or population. The value of the signal may also be compared to a reference value as herein defined. A value more important than a reference value or a control from a healthy tissue is indicative of the presence of angiogenesis and possibly of cancerous cells. The stage of evolution of a cancer may be assessed by comparing in a same subject a signal obtained after two different imaging spaced in time.

In an imaging and/or diagnostic context, the radiolabeled antibody or fragment thereof of the invention is administrated before performing a TEP-CT or SPECT-CT Scan on the subject (typically in the diagnostic sector of a nuclear medicine department).

Kit of Radiotracer

The invention also relates to a kit comprising an antibody or a fragment thereof according to the invention, a chelator, a radioactive element, in three distinct containers, or the antibody or fragment thereof of the invention in a single container and the radioactive element in a distinct container. The kit may further comprise a reducing agent such as for example stannous chloride, a buffer for pH adjustment such as for example sodium acetate or ammonium acetate, and/or a sterile non pyrogenic solution.

The invention also relates to the use of said kit for producing a conjugated and/or labeled antibody or fragment thereof of the invention.

Use of the Labelled Antibody or Fragment Thereof as a Radiotherapeutic Agent

The invention also relates to the use of the antibody or of a fragment thereof of the invention labeled with a radioactive element, typically conjugated to a chelator and labeled with a radioactive element, as a therapeutic agent, typically as a radiotherapeutic agent. Such a therapeutic agent is for use in nuclear medicine, typically in radiotherapy.

The radiolabeled antibody or fragment thereof of the invention advantageously allows a targeted radiotherapy which is typically directed against tissues (over)expressing tumor CD146 protein (i.e. CD146-positive tumor). The radiolabeled antibody or fragment thereof of the invention is able to provide sufficient level of irradiation to targeted cells while not affecting surrounding tissues, typically healthy tissues. Thus, radiation therapy using the radiolabeled antibody or fragment thereof of the invention will allow more specific, effective as well as shorter treatments and will advantageously induce fewer detrimental side effects for the treated patient.

The radioactive element or radionuclide typically used in nuclear medicine therapy is typically a radioactive element having an half-live between 1 day and 75 days such as lutetium 177 (6.64 h), actinium 225 (10 d), lead 212 (10.6 h), bismuth 213 (45 min), yttrium 90 (64.2 h) and Indium 111 (67 h). Beta- or high energy gamma-emitting radionuclides are preferably used in the context of nuclear medicine therapy.

Other characteristics and advantages of the invention are given in the following experimental section (with reference to FIGS. 1 to 3, which should be regarded as illustrative and not limiting the scope of the present application.

BRIEF DESCRIPTION OF THE FIGURES

FIG. 1B. Total CD146 expression was determined by Elisa on lysates of UACC, Panc-1, HUVEC and HMEC-1 cells after 72 h of treatment with control IgG or TsCD146 mAb. Mean values of three different experiments are given.

FIG. 1C. Membrane expression of CD146 was determined by flow cytometry experiments with S-endo1 antibody in the different cell lines after treatment with TsCD146 mAb (5 µg/ml) or IgG (5 µg/ml) for 72 hours. The results are expressed as mean values+/−standard deviation of 3 experiments.

\* $p<0.05$, \*\* $p<0.01$, \*\*\* $p<0.001$, experimental versus control.

Figure 2A:
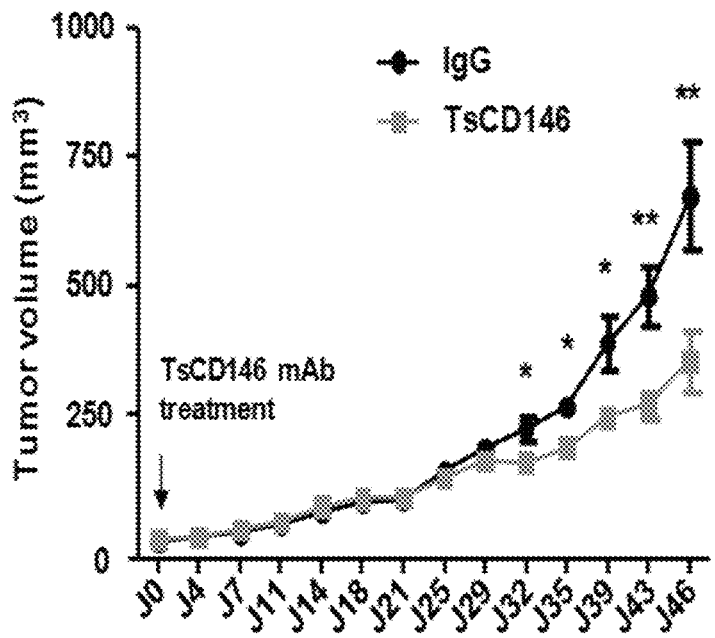
Figure 2B:
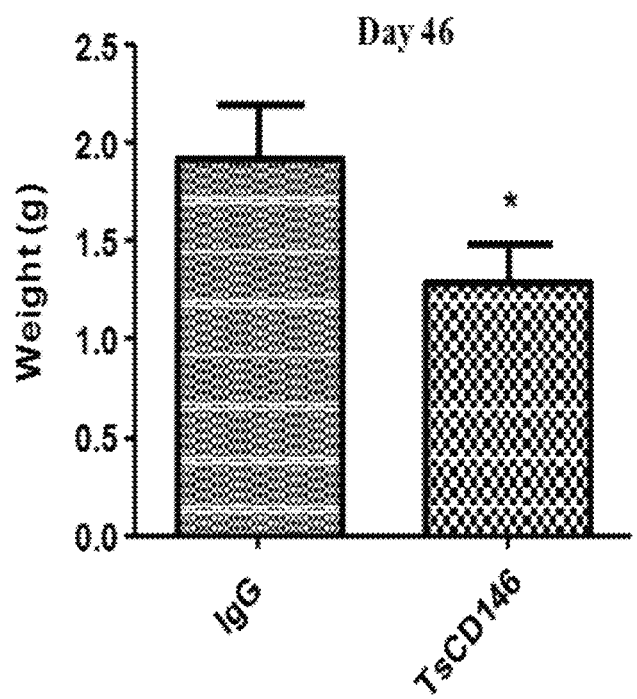
Figure 2C:
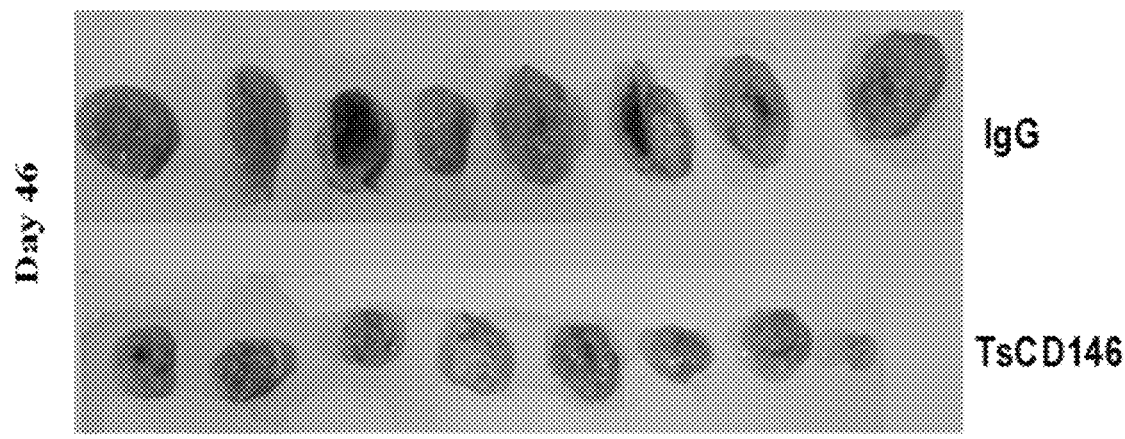

FIGS. 2A-2C: Effect of TsCD146 mAb on growth of C81-61 cells in an animal model of xenograft FIG. 2A. 8 NOD/SCID mice xenografted with C8161 cells were treated for 46 days with control IgG or the TsCD146 mAb. Tumor volume was determined twice a week with caliper.

FIG. 2B. Tumor weight was determined in IgG and TsCD146 mAb treated animals after the sacrifice of the animals.

FIG. 2C. Tumors from IgG and TsCD146 mAb treated animals were photographed after sacrifice of the animals.

Figure 3:
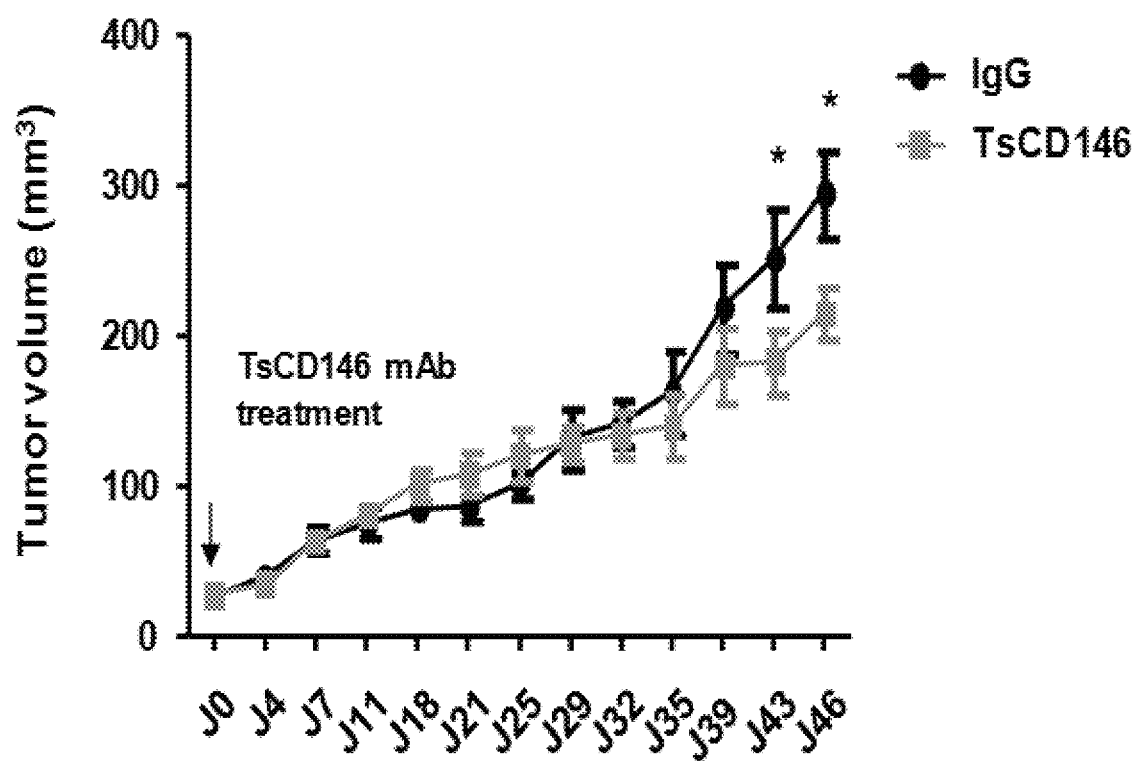

FIG. 3: Effect of TsCD146 mAb on growth of Panc-1 cells in an animal model of xenograft 8 NOD/SCID mice xenografted with Panc-1 cells were treated for 46 days with control IgG or the TsCD146 mAb. Tumor volume was determined twice a week with caliper.

\*: $p<0.05$, experimental versus control.

FIG. 4 relates to a deposited microorganism or other related biological material.

EXPERIMENTAL PART

Inventors have generated antibodies recognizing the CD146 expressed in cancer cells but not CD146 expressed in other cell types. Of interest, one antibody (TsCD146 mAb) displayed these properties. This antibody as well as fragments thereof were thus further characterized in order to evaluate their interest for diagnostic and/or therapeutic applications.

Materials and Methods

Cell Culture

HUVEC (Human Umbilical Vein Endothelial Cells) were grown in Endothelial Cell Growth Media (EGM-2 Bulletkit™) (Lonza, Amboise, France). The HMEC-1 (Human Microvascular Endothelial Cell Line) cell line was grown in Endothelial Basal Medium (EBM) (PAA, Velizy-Villacoublay, France) supplemented with fetal calf serum (FCS 10%), penicillin and streptomycin, (1%), L-glutamine (1%), epidermal growth factor (10 ng/mL) and hydrocortisone (50 µg/mL). HUA-SMC (Smooth Muscle Cells) were grown in Dulbecco's Modified Eagles medium (DMEM) added with 10% SVF.

Tumor cell lines PANC-1 (pancreatic cancer) and LOVO (colon cancer) were cultured in DMEM (Life Technologies, Saint Aubin, France) supplemented with FCS (10%), PS (1%), L-glutamine (1%) and sodium pyruvate (1%). The tumor cell lines UACC-1273 (melanoma), C8161 (melanoma) and SW620 (colon cancer) were cultured in RPMI 1640 Glutamax™ (life technologies) supplemented with FCS (10%) and PS (1%). The cells were grown in a humidified atmosphere with 5% $CO_2$ at 37° C.

Generation of Antibodies Against CD146

Antibodies against CD146 were generated by the platform of monoclonal antibodies (Mi-mAbs; Marseille-Luminy, France) by injection in rat of a recombinant protein, generated in mouse myeloma, corresponding to the extracellular part of CD146. After obtaining the hybridoma, anti-CD146 antibodies were purified by affinity chromatography on a HiTrap protein G column (GE Healthcare). Such an extracellular part of CD146 typically comprises or consists of an amino acid sequence comprising or consisting of a sequence selected from SEQ ID NO: 8, SEQ ID NO: 9, SEQ ID NO: 10, SEQ ID NO: 11, SEQ ID NO: 12, SEQ ID NO: 13, and SEQ ID NO: 14, preferably SEQ ID NO: 14.

qPCR

Cell RNA was extracted using the RNeasy Mini Kit (Qiagen, Hamburg, Germany), according to the supplier's instructions. The extracted RNA was assayed using NanoDrop at 260 nm (Thermo scientific). The reverse transcription (RT) was then carried out with 1 µg of RNA to which is added 10 µL of a mixture (RT buffer, DNX 25×100 mM, RT random primer 10×, multiscribe reverse T, $H_2O$ (Applied Biosystems)). The RT was performed in a thermocycler at 25° C. for 10 minutes, 37° C. for 2 hours, 85° C. for 5 minutes and then at 4° C. 50 ng/µl of cDNA was then taken and placed with 24 µl of a mixture comprising sybergreen (Agilent, Stratagene), right and left primers and $H_2O$. The PCR (Polymerase Chain Reaction) was then carried out using the Step One Plus real-time PCR system (Life Technologies) according to the following profile: 1 cycle of 10 minutes at 95° C. and then 40 cycles of 30 seconds at 95° C. and 1 minute at 60° C. The results were then analyzed using the Step One software. Primers were: GAPDH: R: 5'-GGTGGTCTCCTGACTTCAACA (SEQ ID NO: 15); F: 5'-GTTGCTGTAGCCAATTCGTTGT (SEQ ID NO: 16); CD146: R: 5'-GGCTAATGCCTCAGATCGATG (SEQ ID NO: 17); F: 5'-AATATGGTGTTGAATCTGTCTTG (SEQ ID NO: 18).

Flow Cytometry

After detachment of the cells with trypsin, cells were plated with 0.1% PBS-BSA. Primary antibody (S-endo1, mouse IgG, TsCD146 mAb, rat IgG) was then added to the cells for 45 minutes at 4° C. After rinsing with 0.1%

PBS-BSA, the secondary antibody was added for 45 minutes at 4° C. in the dark. After rinsing with 0.1% PBS-BSA, the cells were taken up in 0.1% PBS-BSA and analyzed by flow cytometer (Gallios™ Flow Cytometer, Beckman Coulter, Villepinte). The results were then analyzed using Kaluza software (Kaluza® Analysis Software, Beckman Coulter).

UACC derived microparticles (MP) were first generated by serial centrifugations (3 centrifugations at 70,000 g for 1 h30) of UACC supernatant medium. MP were then labeled with 10 μl of AnnexinV-FITC (Tau Technologies, Netherlands) and 10 μl of various concentration of PE-TsCD146 mAb during 30 minutes at room temperature, without light. 500 μl of AnnexinV binding buffer were finally added and tube was analysed on flow cytometer. Titration curve was therefore established, by determination of the maximum percentage of double positive AnnexinV/Ts CD146 microparticles among AnnexinV-positive MP (data unshown). The TsCD146 antibody suspension on vesicles was also adjusted equivalently with IgG isotypic control to confirm staining specificity.

The same staining was performed on plasmatic MP derived from healthy patients or patients with melanoma. Briefly, Platelet Free Plasma (PFP) were prepared from EDTA blood collection tubes using a first centrifugation on ficoll sucrose gradient 30 min at 800 g. Then the part above PBMC ring was collected. Then 30 μl of PFP were thawed and stained with AnnexinV FITC and TsCD146 PE Ab or IgG isotypic control during 30 minutes at room temperature, without light. After addition of 500 μl of AnnexinV binding buffer+hirudine (Cryopep, Montpellier, France), 30 μl of MP count beads (Biocytex, Marseille, France) were added to evaluate the tumoral MP concentration.

MP analyses were performed on Gallios Flow Cytometer using the Megamix+FSC strategy previously published by inventors' team (Robert et al., 2012). Cancer MP were defined as AnnexinV/Ts CD146-positive events.

Confocal Microscopy

The cells were seeded on glass plates at 50000 cells per well. At confluence, they were fixed with 4% paraformaldehyde for 15 minutes at room temperature and then rinsed 3 times with PBS Immunofluorescence experiments were then carried out on these cells with the primary anti-CD146 antibodies S-endo1 (Biocytex) and TsCD146 mAb (dilution 1/200), for 1 hour in a humid chamber in the dark, then with the secondary anti-mouse and anti-rat (dilution 1/200) antibodies coupled to Alexa 488 diluted in PBS-saponin (0.2%)—FCS (10%) for 30 minutes. The lamellae were then mounted with DAPI (Prolong® gold antifade reagent with DAPI, Invitrogen) mounting liquid and observed with the confocal microscope (Leica SP5, Leica, Nanterre, France).

For experiments on biopsies, organs were fixed in 4% formalin and cut using a cryostat. The slides were then pretreated in a pH 6 citrate buffer at 96° C. for 30 minutes. They were then preincubated for 30 minutes in PBS-BSA 0.5%-Triton 10×0.1% Immunofluorescence experiments were then carried out on these sections with primary antibodies S-endo1 and TsCD146 mAb (dilution 1/100) overnight in a humidity chamber and anti-mouse and anti-rat secondary antibodies (dilution 1/200) coupled to Alexa diluted in PBS-BSA 0.5%-Triton 10×0.1% for 1 hour. The lamellae were then mounted with mounting fluid (Prolong, Invitrogen) and observed with the confocal microscope (Leica SP5).

For experiments with rab11, cells were first treated for 72 hours with TsCD146 mAb. Then cells were fixed with PFA 4% and incubated for 5 minutes in PBS-Triton 10×0.2% followed by 30 minutes incubation with PBS-BSA 0.5%. They were then incubated with rab11 antibody (Abcam, Ab3612) for 1 hour and secondary antibodies (anti-rat alexa 647 for TsCD146 mAb and anti-rabbit alexa 488 for rab 11) for 1 hour. Colocalization of both proteins was visualized with confocal microscope.

CD146 Elisa

Total CD146 expression was determined on the different cell lines using the CD146 Elisa kit (Biocytex), as recommended by the manufacturer.

Immunoprecipitation and Western-Blot Experiments

Immunoprecipitation of CD146 was performed by incubating 5 μg of TsCD146 or S-Endo1 antibodies overnight in cell lysates (Lysis buffer was: 120 mM NaCl, 10 mM Tris HCl pH 7.5, 2 mM EDTA, 1% Triton, 25 mM KCl). Protein A sepharose was then added in the lysate before centrifugation, and denaturation with NuPAGE sample-reducing agent (Invitrogen). Samples were then subjected to NuPAGE using 4-12% Novex Bis-Tris gels (Invitrogen) and separated proteins were transferred onto nitrocellulose membranes (Invitrogen). Membranes were probed with COM 7A4 (Biocytex) anti-CD146 diluted 1/1000 followed by secondary antibodies coupled to peroxidase. Blots were revealed with the ECL substrate (Pierce).

Proliferation Experiments

The different cell lines were seeded in 96-well plates at 10,000 cells per well. 12 hours later, the rat control IgG or TsCD146 mAb was added at the indicated concentration for 72 hours. After 48 hours, BrdU (BromodeoxyUridine) was added for 24 h. The proliferation was analyzed using the "Cell proliferation ELISA, BrdU" kit (Roche Diagnostics, Meylan, France), according to the supplier's instructions. The reaction was then stopped with a solution of 1M $H_2SO_4$. The absorbance was read at 450 nm using a microplate photometer.

Internalization Experiments with Protonex Red 600 SE

Cells were seeded in 96-well plates, 10,000 cells per well, in complete cell culture medium containing 2.5-30 μg/ml Ts CD146 mAb conjugated to Protonex red 600 SE (AAT Bioquest, CA). Protonex is a pH-sensitive dye that is non-fluorescent at basic pH (extracellular: culture medium) and fluorescent at acidic pH (intracellular: endosomes, lysosomes). Serially-diluted antibodies were added and plates were incubated at 37° C. for 3, 6 and 9 hours. Experiments were also performed at 4° C. as a control in order to block the internalization processes. Mean fluorescent intensities (MFI) of intracellular Protonex were measured per well using Glomax (Promega).

Analysis of Tumor Growth on Tumor Xenografted Animals

Xenografts of human tumor cell lines were produced by injecting tumor cells ($5 \times 10^6$ cells resuspended in PBS) subcutaneously into the back of NOD/SCID mice. When tumors reached 20 $mm^3$, peri-tumoral administration of purified TsCD146 mAb or rat control IgG were performed at a dose of 10 μg, twice a week, for 46 days. Tumor size was measured twice a week with caliper and tumor volume was determined according to the equation:

(length*width*thickness)*0.5236. Tumor weight was also evaluated at the end of the experiment after the sacrifice of the animal.

NODAGA Conjugation and Radiolabeling

TsCD146 Fab'2 were generated and purified with Amicon Ultra-0.5 3 KDa Centrifugal Filter 500 μL (Millipore Corporation) and added 10 equivalents of p-NCS-benzyl-NODAGA in 0.2M bicarbonate buffered. The mixture was left at 37° C. for 3 h. The conjugate was then transferred to an Amicon Ultra-0.5 3 KDa Centrifugal Filter Devices 500 μL, washed 3 times with PBS to eliminate small molecules which did not react, concentrated in distilled water (0.5 mg/mL) and stored at −80° C.

Radiochemistry

Gallium was obtained in $^{68}GaCl_3$ form using a commercial $TiO_2$-based $^{68}Ge/^{68}Ga$ generator (Obninsk). $^{68}GaCl_3$ (200.69±40.97 MBq/0.5 mL) was eluted from a $^{68}Ge$-$^{68}Ga$ generator using 0.1 N HCl, after which 4M ammonium acetate buffer (pH 7.4) was added. This solution was then added to NODAGA-TsCD$_{146}$ Fab'2 (15 µg); final pH of the mixture was 6.0. The reaction mixture was stirred at room temperature for 15 min with manual shaking.

Determination of radiochemical purity was done by radio-thin-layer chromatography (ITLC_SG) and was performed using a Ray-test miniGITA radio-TLC scanner detector (Straubenhardt, Ge) (eluents, 1:1 [v/v] mixture of 1M aqueous ammonium acetate solution and methanol, RF $^{68}Ga/^{68}Ga$-NODAGA-TsCD146 Fab'2: 0/1).

MicroTEP Imaging

Mice xenografted with C8161 cells (n=6) were injected IV at day 36 post implementation with 5-10 MBq of $^{68}Ga$-NODAGA-TsCD146 Fab'2 under 2% isoflurane anesthesia. PET images were acquired 1 h30 and 3H00 after $^{68}Ga$-NODAGA-TsCD146 Fab'2 IV injection with a MedisoNanoPET/CT under 2% isoflurane anesthesia.

Ethics Committee Approval.

The animal experiments conformed to the directive 2010/63/EU of the European Parliament and were approved by the Institution's Animal care and Use Committee (Aix-Marseille University). The procedures described above were conducted under an institutional approved animal use protocol (Marseille Ethical Committee) and under the supervision of an authorized researcher (B. Guillet; no 13328).

Statistical Analysis and Expression of Results

The data were expressed as mean values±SEM of the indicated number of experiments. Statistical analysis was performed with the Prism software (GraphPad Software Inc., San Diego, Calif., USA). The variance between the different groups to be compared was estimated before statistical analysis. When comparing more than two groups, a non-parametric one-way ANOVA followed by a Dunn's multiple comparison test was used. Significant differences between two groups were determined using the unpaired student's t test or Mann-Whitney test. A value of $P≤0.05$ was considered to be significant.

The sample size was chosen for each type of experiment using an a priori power analysis. No exclusion criteria were taken into account; all the values obtained during the experiments were used for both in vitro and in vivo studies. In animal studies, the groups' sizes were chosen using an a priori power analysis, the investigator was blinded to the group allocation and mice were distributed at random in the different groups.

Results

Generation of a Newly Developed Monoclonal Anti-CD146 Antibody Specifically Targeting Tumor CD146.

The recombinant extracellular part of CD146 was produced in mouse myeloma cells and used as immunogen to generate rat monoclonal antibodies. Hybridomas were screened for clones producing antibodies that i/bind the CD146 expressed by cancer cells, and ii/do not bind to the CD146 expressed on the surface of endothelial and smooth muscle cells. The hybridoma clone TsCD146 mAb (IgG1 subtype) was selected on these criteria and was further characterized.

Characterization of TsCD146 mAb

Since it has been shown that many tumors express CD146, inventors examined the expression of the molecule in five cancer lines with reference to two types of micro- and macrovascular endothelial cells, and smooth muscle cells. CD146 expression was evaluated in these different cells at the mRNA level by RT-PCR with primers directed against the extracellular portion of CD146 and at the protein level by Elisa assay on cell lysates. UACC-1273 and C8161, two metastatic melanoma cell lines; Panc-1, a pancreatic cancer line; SW620 and Lovo, two colon cancer lines were used. In these different cancer cell lines, only Lovo do not express CD146. For endothelial cells, HUVECs which are macroendothelial primary cells and the HMEC-1 line which is a microendothelial cell line were used. Finally, the HUA-SMC smooth muscle cells were also used. In all the cells, except Lovo, inventors observed CD146 expression both at the mRNA and protein levels. TsCD146 mAb was characterized in comparison to the commercially available S-Endo1 antibody on its ability to bind cancer cells, endothelial cells and smooth muscle cells. To this end, both flow cytometry and immunofluorescence experiments were performed. Results show that the TsCD146 mAb was able to bind UACC-1273, Panc-1, C8161, SW620 cancer cells and not Lovo cells which do not express CD146. In contrast, it was not able to bind HUVEC, HMEC-1 and HUA-SMC cells. As a control, the S-Endo1 antibody was able to bind all cells, except Lovo cells. In addition, immunoprecipitation experiments were performed on the different cell lines with the TsCD146 mAb and CD146 was revealed by western-blot. Results show that TsCD146 mAb immunoprecipitates CD146 only in UACC and Panc-1 cell lines, but not in HUVEC and HMEC-1 cells, and that the molecule is evidenced around 110 kDa.

Use of TsCD146 mAb for Immunodetection of Cancer Cells in Biopsies of Human Tissues In order to demonstrate that TsCD146 mAb detects tumor but not vascular cells, inventors carried out immunofluorescence experiments on human biopsies of melanoma, renal carcinoma and colon adenocarcinoma. Sections of tissues were also labeled with an antibody directed against the vascular endothelium (anti-CD31 antibody). Binding of TsCD146 mAb was evidenced on tumor cells but not on endothelial cells which were labeled with CD31 mAb. In contrast, S-Endo1 antibody was able to bind both tumor and endothelial cells in renal carcinoma, as demonstrated by its colocalization with CD31 antibody in vessels.

Use of Radiolabeled TsCD146 Fab'2 for Immunodetection of Melanoma Cells by PET Imaging Inventors investigated whether TsCD146 mAb was able to detect human melanoma cells in vivo using a xenograft model. To this end, the inventors used Fab'2 fragment from TsCD146 mAb coupled to $^{68}Ga$ (see Material and Methods). Nude mice were injected with C8161 cells and 36 days after, $^{68}Ga$ Fab'2-TsCD146 was injected in animals. Results obtained by PET imaging showed that the tumor was visualized by the radiolabeled Fab'2. Of interest, only the external part of the tumor was labeled, without labeling in the central part. To further analyze this result, inventors performed immunofluorescence and histological experiments on these tumors after the sacrifice of the animal. Results confirmed the results obtained in vivo. Indeed, only the external part of the tumor was labeled with the TsCD146 mAb and the internal part corresponded to necrotic tissues.

Figure 1A:
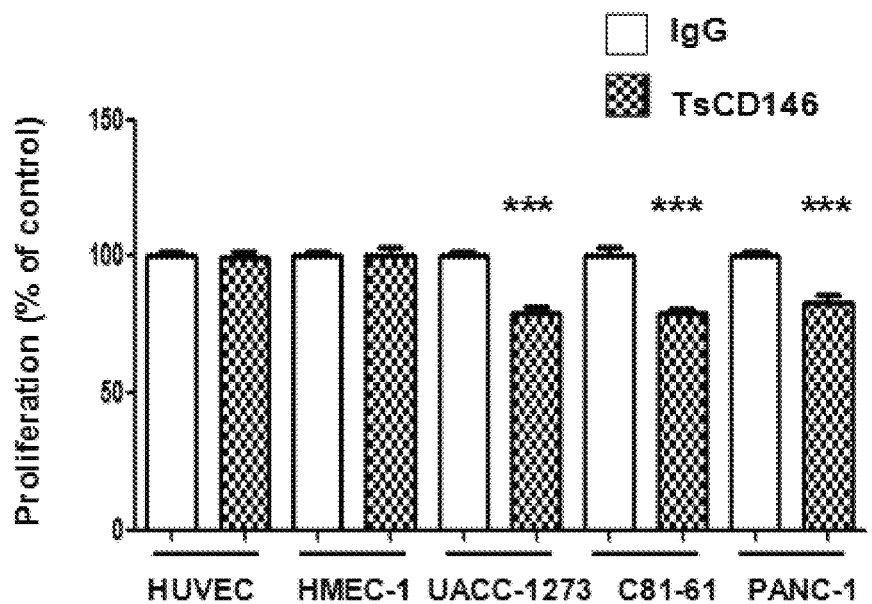
FIGS. 1A-1C: Effect of TsCD146 mAb antibody on cell proliferation and CD146 expression FIG. 1A. Analysis of the proliferation of HUVEC, HMEC-1, UACC-1273, C81-61 and Panc-1 cells after 72 h in the presence of IgG or TsCD146 mAb (5 µg/ml). The results are expressed as mean values+/−standard deviation of 3 experiments.

TsCD146 mAb Decreases Cancer Cell Proliferation and CD146 Expression in the Membrane Cancer Cells by Internalizing the Molecule The inventors tested the effect of TsCD146 mAb on cancer cell proliferation as compared to proliferation of endothelial cells. After a 72-hour treatment with the antibody at 5 µg/ml, the inventors observed a decrease in proliferation of UACC-1273, C8161 and Panc-1 cells whereas there was no effect on HUVEC and HMEC-1 cells (FIG. 1A).

Figure 1B:
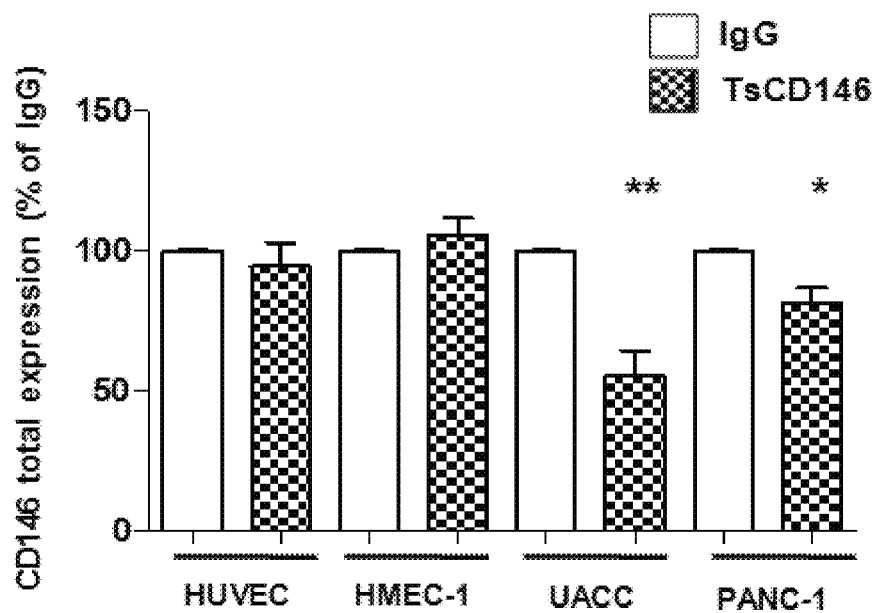
Figure 1C:
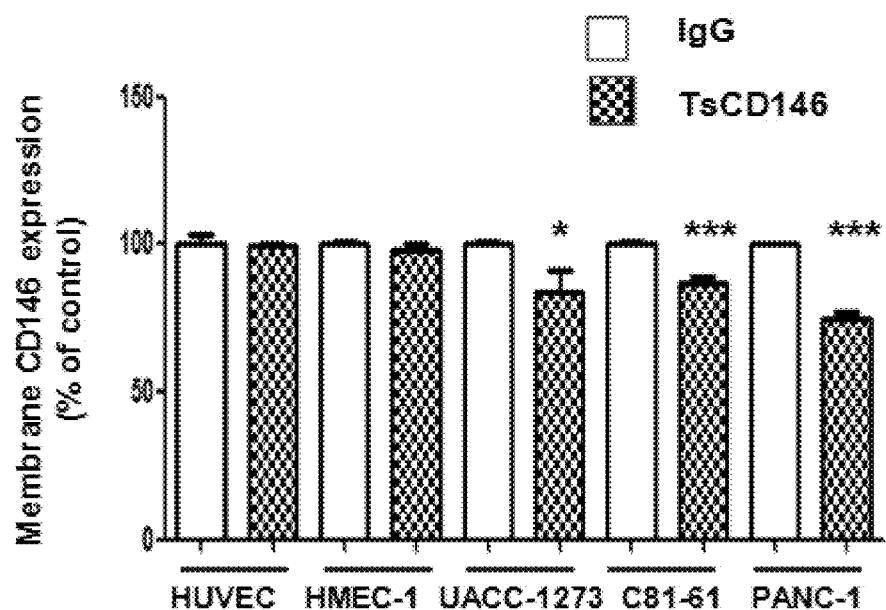

Since an anti-proliferative effect of TsCD146 mAb was observed on cancer cells and since CD146 is involved in cell proliferation, the inventors investigated whether this effect could be due to a decrease in the expression of CD146. In a first series of experiments, they analyzed the total expression of CD146 by Elisa on whole cell lysates. Results (FIG. 1B) showed that total CD146 was reduced in cancer cells but not in endothelial cells after 72 h of treatment with TsCD146 mAb. In a second series of experiments, inventors then investigated whether this could be due to a decrease in the membrane expression of CD146. The membrane CD146 expression was thus evaluated by flow cytometry in cancer cells after 72 hours of treatment with the TsCD146 mAb or the control IgG. A significant decrease in membrane expression of CD146 was observed in the different cancer cell lines whereas there was no effect in endothelial cells (FIG. 1C).

In view of these results, inventors performed experiments to determine whether this down-regulation of membranous CD146 was due to membranous CD146 internalization and degradation. To this end, they used a probe that was fluorescent in acidic subcellular compartments as endosomes or lysosomes. Results show that after treatment of C81-61 cells with the TsCD146 mAb, CD146 was directed towards intracellular acidic compartments of the cells at 37° C. but not at 4° C., this last condition preventing the internalization of proteins from the membrane to the intracellular compartments. In addition, time-course experiments showed that the phenomenon started rapidly since it could be observed as soon as three hours after the beginning of treatment with the TsCD146 mAb. Similar results were obtained with Panc-1 and UACC cells. This result was confirmed by confocal microscopy experiments. Indeed, inventors showed that, after 72 h of treatment with TsCD146 mAb, CD146 was colocalized with rab11 in intracellular compartments in C81-61 cells.

TsCD146 mAb Decreases Tumor Growth in Animal Models of Xenograft

The effect of TsCD146 mAb was tested on tumor growth in C8161 melanoma cells orthotopically xenografted in NOD/SCID mice. When tumors reached about 20 mm$^3$, TsCD146 mAb or an isotype control IgG (rat IgG1 mAb) were injected, twice a week, for 46 days. Tumor growth was monitored by determination of relative tumor volume by caliper. Caliper measurement revealed a significant decrease of tumor size in the group of mice injected with the TsCD146 mAb as compared to the rat IgG control group after 32 days of treatment (FIG. 2A). Tumor weight was also determined at day 46 on isolated tumors after the sacrifice of animals and revealed that tumor weight was significantly reduced in the TsCD146 mAb treated group as compared to the rat IgG control group (FIG. 2B). Finally, tumors were photographed at day 46 after the sacrifice of the animals and confirmed the inhibitory effect of TsCD146 mAb (FIG. 2C).

These results were confirmed in another model of CD146-positive tumors subcutaneously xenografted in nude mice, the Panc-1 cells. Using the same experiments, inventors showed that tumor volume measured with caliper was significantly reduced in the TsCD146 mAb treated tumor group as compared to the control group from day 43 after the beginning of the treatment (FIG. 3).

Discussion

Up to now, it was impossible to specifically target CD146 expressed by cancer cells or their derivatives as circulating cancer cells or microparticles, leading to major problems for diagnosis and/or targeted therapy. Thanks to the present invention, specifically targeting the tumor form of CD146 with an antibody or a fragment thereof is possible and allows detecting and targeting tumor cells without affecting vascular or immune integrity and functions.

Concerning the interest of TsCD146 mAb and fragment F(ab')2 for diagnosis, the inventors have shown that it is able to detect CD146 in human biopsies of different tumors and in vivo in xenografted tumors by PET imaging. Concerning this last technique, it will be useful for the specific detection of CD146-positive tumors before targeted therapy. Today, tumor cells are detected by imaging with common markers as $^{18}$FDG which do not permit to distinguish between tumors (Singnurkar et al., 2017). There is a need for new biomarkers able to discriminate between tumors thereby allowing personalized medicine. The TsCD146 mAb and its F(ab')2 fragment constitute such biomarkers.

In addition to the diagnostic interest, inventors show that TsCD146 mAb is of great interest for therapeutic purposes. Indeed, results demonstrate that treatment with the antibody induces a decrease in the expression of the tumor CD146 molecule. This is due in part to an internalization of the membranous molecule after treatment with the antibody, as demonstrated by the use of a pH-dependent fluorescent dye and the colocalization with rab11, which is involved in vesicle transport between membrane and intracellular compartments (Welz et al., 2014). This mechanism has been described for other antibodies, as trastuzumab. This antibody is currently used for the treatment of breast cancer and internalizes the HER2 receptor, a marker of bad prognosis as CD146 (Zum et al., 2002). Thus, the tumor CD146 molecule can be removed from the plasma membrane and then be directed from the endosomal to the lysosomal compartments where it is degraded. Moreover, in xenografted models of cancer cells, inventor's experiments showed that TsCD146 mAb administration leads to a significant decrease in tumor growth. In view of its mechanism of action, TsCD146 mAb is of therapeutic interest, administered either alone or coupled to toxins or radioactive atoms, in order to fight cancer cells.

Conclusion

In conclusion, the herein provided data demonstrate that it is possible to specifically target the CD146 molecule expressed by tumor cells (also herein identified as "tumor CD146" or "tumor CD146 protein"). For the first time, inventors have successfully generated a monoclonal antibody, herein referred to as TsCD146 mAb, as well as fragments thereof, in particular a F(ab')2 fragment, that specifically bind and internalize tumor membranous CD146. This antibody is of interest in diagnosis since it is able to recognize CD146-positive tumors on biopsies and in vivo by PET imaging. In addition, because of its mechanism of action, this antibody is of interest in therapy since it is able to reduce the growth of CD146-positive tumors xenografted in nude mice.

REFERENCES

Bardin N, Anfosso F, Masse J M et al. Identification of CD146 as a component of the endothelial junction involved in the control of cell-cell cohesion. Blood 2001; 98(13): 3677-84.

Bardin N, Blot-Chabaud M, Despoix N et al. CD146 and its soluble form regulate monocyte transendothelial migration. Arterioscler Thromb Vasc Biol. 2009; 29(5): 746-53.

Bardin N, Frances V, Lesaule G et al. Identification of the S-Endo 1 endothelial-associated antigen. Biochem Biophys Res Commun. 1996; 218(1): 210-6.

Bardin N, Moal V, Anfosso F et al. Soluble CD146, a novel endothelial marker, is increased in physiopathological settings linked to endothelial junctional alteration. Thromb Haemost. 2003; 90(5): 915-20.

De Souza P S, Faccion R S, Bernardo P S et al. Membrane microparticles: shedding new light into cancer cell communication. J Cancer Res Clin Oncol. 2016; 142(7): 1395-406.

Dignat-George F, Boulanger C M. The many faces of endothelial microparticles. Arterioscler Thromb Vasc Biol. 2011; 31(1):27-33.

Duan H, Xing S, Luo Y et al. Targeting endothelial CD146 attenuates neuroinflammation by limiting lymphocyte extravasation to the CNS. Sci Rep. 2013; 3: 1687.

Imbert AM1, Garulli C, Choquet E, Koubi M, Aurrand-Lions M, Chabannon C. CD146 expression in human breast cancer cell lines induces phenotypic and functional changes observed in Epithelial to Mesenchymal Transition. PLoS One. 2012; 7(8):e43752.

Kebir A, Harhouri K, Guillet B et al. CD146 short isoform increases the proangiogenic potential of endothelial progenitor cells in vitro and in vivo. Circ Res. 2010; 107(1): 66-75.

Lehmann J M, Riethmüller G and Johnson J P. MUC18, a marker of tumor progression in human melanoma, shows sequence similarity to the neural cell adhesion molecules of the immunoglobulin superfamily. Proc Natl Acad Sci USA. 1989; 86(24): 9891-5.

Lin Y, Wu X, Shen Y et al. A novel antibody AA98 V(H)/L directed against CD146 efficiently inhibits angiogenesis. Anticancer Res. 2007; 27(6B): 4219-24.

Maitra A, Hansel D E, Argani P et al. Global expression analysis of well-differentiated pancreatic endocrine neoplasms using oligonucleotide microarrays. Clin Cancer Res. 2003; 9: 5988-95.

Mills L, Tellez C, Huang S et al. Fully human antibodies to MCAM/MUC18 inhibit tumor growth and metastasis of human melanoma. Cancer Res. 2002; 62(17): 5106-14.

Pickl W F, Majdic O, Fischer G F, Petzelbauer P, Faé I, Waclavicek M, Stöckl J, Scheinecker C, Vidicki T, Aschauer H, Johnson J P, Knapp W. MUC18/MCAM (CD146), an activation antigen of human T lymphocytes. J Immunol 1997 158(5): 2107-15.

Robert S, Lacroix R, Poncelet P et al. High-sensitivity flow cytometry provides access to standardized measurement of small-size microparticles. Arterioscler Thromb Vasc Biol. 2012; 32(4): 1054-8.

Sers C, Kirsch K, Rothbächer U et al. Genomic organization of the melanoma-associated glycoprotein MUC18: implications for the evolution of the immunoglobulin domains. Proc Natl Acad Sci USA. 1993; 90(18): 8514-8.

Shih I M. The role of CD146 (Mel-CAM) in biology and pathology. J Pathol. 1999; 189(1):4-11.

Singnurkar A, Poon R, Metser U. Comparison of 18F-FDG-PET/CT and 18F-FDG-PET/MR imaging in oncology: a systematic review. Ann Nucl Med. 2017; 28: 1-13.

Stalin J, Nollet M, Garigue P et al. Targeting soluble CD146 with a neutralizing antibody inhibits vascularization, growth and survival of CD146-positive tumors. Oncogene. 2016; 35(42): 5489-5500.

Ueno K, Hirata H, Majid S et al. IGFBP-4 activates the Wnt/beta-catenin signaling pathway and induces M-CAM expression in human renal cell carcinoma. Int J Cancer. 2011; 129(10): 2360-9.

Wang Z, Yan X. CD146, a multi-functional molecule beyond adhesion. Cancer Lett. 2013; 330(2): 150-62.

Welz T, Wellbourne-Wood J, Kerkhoff E Orchestration of cell surface proteins by Rab11. Trends Cell Biol. 2014; 24(7):407-15.

Wu G J, Fu P, Chiang C F et al. Increased expression of MUC18 correlates with the metastatic progression of mouse prostate adenocarcinoma in the TRAMP model. J Urol. 2005; 173(5): 1778-83.

Zeng G F, Cai S X and Wu G J. Up-regulation of METCAM/MUC18 promotes motility, invasion, and tumorigenesis of human breast cancer cells. BMC Cancer. 2011; 11:113-126.

Zum Büschenfelde CM, Hermann C, Schmidt B et al. Antihuman epidermal growth factor receptor 2 (HER2) monoclonal antibody trastuzumab enhances cytolytic activity of class I-restricted HER2-specific T lymphocytes against HER2-overexpressing tumor cells. Cancer Res. 2002; 62(8): 2244-7.

The invention claimed is:

1. An antibody or a fragment thereof which is directed against a CD146 protein, wherein said antibody or fragment comprises light chain variable region (VL) CDR polypeptide sequences comprising SEQ ID NO: 1, sequence NAN and SEQ ID NO: 2, and heavy chain variable region (VH) CDR polypeptide sequences comprising SEQ ID NO: 3, SEQ ID NO: 4 and SEQ ID NO: 5.

2. The antibody or fragment thereof according to claim 1, wherein the sequence of the light chain variable region (VL) comprises the sequence of SEQ ID NO: 6 and wherein the sequence of the heavy chain variable region (VH) comprises the sequence of SEQ ID NO: 7.

3. The antibody according to claim 1, wherein said antibody is a monoclonal antibody.

4. The antibody according to claim 3, wherein said antibody is produced by the hybridoma deposited on Apr. 10, 2017 at the Collection Nationale de Cultures de Microorganismes (CNCM) under the number CNCM I-5246.

5. A hybridoma deposited on Apr. 10, 2017 at the Collection Nationale de Cultures de Microorganismes (CNCM) under the number CNCM I-5246.

6. A nucleic acid molecule encoding an antibody or a fragment thereof according to claim 1.

7. A vector comprising a nucleic acid molecule according to claim 6.

8. A host cell comprising a nucleic acid molecule according to claim 6 or a vector comprising said nucleic acid molecule.

9. A pharmaceutical composition comprising a pharmaceutically acceptable carrier and at least one compound selected from the group consisting of: an antibody and/or a fragment thereof according to claim 1; a nucleic acid encoding said an antibody and/or a fragment thereof; a vector comprising said nucleic acid; and a host cell comprising said nucleic acid.

10. A method of treating cancer comprising administering an antibody and/or a fragment thereof according to claim 1, or a pharmaceutical composition thereof, to a subject having cancer.

11. The method according to claim 10, wherein the cancer is selected from melanoma, kidney cancer, pancreatic cancer and colon cancer.

12. An in vitro diagnostic and/or prognostic method of detecting cancer in a subject wherein said method comprises a step of determining CD146 protein expression and/or level of expression in a biological sample of said subject using at least one antibody and/or a fragment thereof according to claim 1, the detection of CD146 protein expression or levels indicating the presence of cancer in said subject.

13. An in vitro method for monitoring the response to an anticancer treatment of a subject suffering from cancer comprising determining CD146 protein level of expression in a biological sample of said subject using at least one antibody and/or a fragment thereof according to claim 1 at two or more time points during said anticancer treatment, wherein an equal or higher CD146 protein level of expression in a biological sample of the subject at a later time point, compared to a reference value obtained in a biological sample of the subject at an earlier time point, is indicative of a resistance of the subject to said anticancer treatment whereas a lower CD146 protein level is indicative of a response of the subject to said anticancer treatment.

14. A kit comprising at least one antibody and/or a fragment thereof as defined in claim 1 and, at least one reagent for detecting said at least one antibody and/or fragment thereof.

15. A method of imaging a subject comprising administering to the subject a radiolabeled antibody or a fragment thereof according to claim 1, performing an imaging method on said subject, and determining or analyzing the presence and/or amount of said radiolabeled antibody or fragment thereof present in the subject.

16. The method according to claim 15, wherein the imaging comprises Single Photon Emission Computed Tomography (SPECT-CT) or Positron Emission Tomography-Computed Tomography (PET-CT).

17. The antibody or fragment thereof according to claim 1, wherein said antibody or fragment thereof is conjugated to a drug.

18. The antibody or fragment thereof according to claim 17, wherein the drug is Monomethyl Auristatin E (MMAE).

19. The antibody or fragment thereof according to claim 1, wherein said antibody or fragment thereof is human or humanized.

* * * * *

SEQUENCE LISTING

```
<160> NUMBER OF SEQ ID NOS: 18

<210> SEQ ID NO 1
<211> LENGTH: 6
<212> TYPE: PRT
<213> ORGANISM: artificial sequence
<220> FEATURE:
<223> OTHER INFORMATION: Light Chain CDR1

<400> SEQUENCE: 1

Gln Asn Ile Tyr Lys Asn
1               5

<210> SEQ ID NO 2
<211> LENGTH: 8
<212> TYPE: PRT
<213> ORGANISM: artificial sequence
<220> FEATURE:
<223> OTHER INFORMATION: Light Chain CDR3

<400> SEQUENCE: 2
```

```
Gln Gln Tyr Tyr Ser Gly Trp Thr
1               5

<210> SEQ ID NO 3
<211> LENGTH: 9
<212> TYPE: PRT
<213> ORGANISM: artificial sequence
<220> FEATURE:
<223> OTHER INFORMATION: Heavy Chain CDR 4

<400> SEQUENCE: 3

Ser Gly Phe Thr Phe Ser Asn Tyr Gly
1               5

<210> SEQ ID NO 4
<211> LENGTH: 8
<212> TYPE: PRT
<213> ORGANISM: artificial sequence
<220> FEATURE:
<223> OTHER INFORMATION: Heavy Chain CDR 5

<400> SEQUENCE: 4

Tyr Ile Ser His Asp Gly Gly Ser
1               5

<210> SEQ ID NO 5
<211> LENGTH: 10
<212> TYPE: PRT
<213> ORGANISM: artificial sequence
<220> FEATURE:
<223> OTHER INFORMATION: Heavy Chain CDR 6

<400> SEQUENCE: 5

Asp Thr Thr Asp Tyr Tyr Phe Asp Tyr Trp
1               5                   10

<210> SEQ ID NO 6
<211> LENGTH: 106
<212> TYPE: PRT
<213> ORGANISM: artificial sequence
<220> FEATURE:
<223> OTHER INFORMATION: Full VL region

<400> SEQUENCE: 6

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Asn Ile Tyr Lys Asn
            20                  25                  30

Leu Ala Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Glu Leu Thr Leu Thr Ile Ser Ser Leu Gln Pro
65                  70                  75                  80

Glu Asp Val Ala Thr Tyr Phe Cys Gln Gln Tyr Tyr Ser Gly Trp Thr
                85                  90                  95

Phe Gly Gly Gly Thr Lys Leu Glu Leu Lys
            100                 105

<210> SEQ ID NO 7
<211> LENGTH: 118
<212> TYPE: PRT
<213> ORGANISM: artificial sequence
```

<220> FEATURE:
<223> OTHER INFORMATION: VH full region

<400> SEQUENCE: 7

Glu Glu Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Asn Tyr
            20                  25                  30

Gly Met Ala Trp Val Arg Gln Ala Pro Lys Lys Gly Leu Glu Trp Val
        35                  40                  45

Ala Tyr Ile Ser His Asp Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Asp Thr Thr Asp Tyr Tyr Phe Asp Tyr Trp Gly Gln Gly Val
            100                 105                 110

Met Val Thr Val Ser Ser
            115

<210> SEQ ID NO 8
<211> LENGTH: 552
<212> TYPE: PRT
<213> ORGANISM: Homo sapiens
<220> FEATURE:
<223> OTHER INFORMATION: CD146 sequence 1

<400> SEQUENCE: 8

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu

```
                    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                    245                 250                 255

Glu Pro Val Gly Met Leu Lys Glu Gly Asp Arg Val Glu Ile Arg Cys
                260                 265                 270

Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
                435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
530                 535                 540

Ser Thr Ser Thr Glu Arg Lys Leu
545                 550

<210> SEQ ID NO 9
<211> LENGTH: 553
<212> TYPE: PRT
<213> ORGANISM: Homo sapiens
<220> FEATURE:
<223> OTHER INFORMATION: CD146 sequence 2

<400> SEQUENCE: 9

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
```

-continued

```
            20                  25                  30
Pro Glu Leu Val Glu Val Glu Val Gly Ser Thr Ala Leu Leu Lys Cys
            35                  40                  45
Gly Leu Ser Gln Ser Gln Gly Asn Leu Ser His Val Asp Trp Phe Ser
        50                  55                  60
Val His Lys Glu Lys Arg Thr Leu Ile Phe Arg Val Arg Gln Gly Gln
 65                 70                  75                  80
Gly Gln Ser Glu Pro Gly Glu Tyr Glu Gln Arg Leu Ser Leu Gln Asp
                85                  90                  95
Arg Gly Ala Thr Leu Ala Leu Thr Gln Val Thr Pro Gln Asp Glu Arg
               100                 105                 110
Ile Phe Leu Cys Gln Gly Lys Arg Pro Arg Ser Gln Glu Tyr Arg Ile
               115                 120                 125
Gln Leu Arg Val Tyr Lys Ala Pro Glu Glu Pro Asn Ile Gln Val Asn
           130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
               165                 170                 175
Asn Gly Arg Pro Leu Lys Glu Glu Lys Asn Arg Val His Ile Gln Ser
           180                 185                 190
Ser Gln Thr Val Glu Ser Ser Gly Leu Tyr Thr Leu Gln Ser Ile Leu
       195                 200                 205
Lys Ala Gln Leu Val Lys Glu Asp Lys Asp Ala Gln Phe Tyr Cys Glu
   210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
               245                 250                 255
Glu Pro Val Gly Met Leu Lys Glu Gly Asp Arg Val Glu Ile Arg Cys
           260                 265                 270
Leu Ala Asp Gly Asn Pro Pro His Phe Ser Ile Ser Lys Gln Asn
       275                 280                 285
Pro Ser Thr Arg Glu Ala Glu Glu Thr Thr Asn Asp Asn Gly Val
   290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Leu Ser Glu Pro Gln
               325                 330                 335
Glu Leu Leu Val Asn Tyr Val Ser Asp Val Arg Val Ser Pro Ala Ala
           340                 345                 350
Pro Glu Arg Gln Glu Gly Ser Ser Leu Thr Leu Thr Cys Glu Ala Glu
       355                 360                 365
Ser Ser Gln Asp Leu Glu Phe Gln Trp Leu Arg Glu Glu Thr Asp Gln
   370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
               405                 410                 415
Leu Asn Arg Thr Gln Leu Val Lys Leu Ala Ile Phe Gly Pro Pro Trp
           420                 425                 430
Met Ala Phe Lys Glu Arg Lys Val Trp Val Lys Glu Asn Met Val Leu
       435                 440                 445
```

```
Asn Leu Ser Cys Glu Ala Ser Gly His Pro Arg Pro Thr Ile Ser Trp
        450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
        530                 535                 540

Ser Thr Ser Thr Glu Arg Lys Leu Pro
545                 550

<210> SEQ ID NO 10
<211> LENGTH: 554
<212> TYPE: PRT
<213> ORGANISM: Homo sapiens
<220> FEATURE:
<223> OTHER INFORMATION: CD146 sequence 3

<400> SEQUENCE: 10

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Glu Pro Asn Ile Gln Val Asn
        130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
        210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255
```

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
                355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
                435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
                515                 520                 525

Thr Thr Gly Leu Ser Thr Ser Thr Ala Ser Pro His Thr Arg Ala Asn
                530                 535                 540

Ser Thr Ser Thr Glu Arg Lys Leu Pro Glu
545                 550

<210> SEQ ID NO 11
<211> LENGTH: 555
<212> TYPE: PRT
<213> ORGANISM: Homo sapiens
<220> FEATURE:
<223> OTHER INFORMATION: CD146 sequence 4

<400> SEQUENCE: 11

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

```
Val His Lys Glu Lys Arg Thr Leu Ile Phe Arg Val Arg Gln Gly Gln
 65                  70                  75                  80

Gly Gln Ser Glu Pro Gly Glu Tyr Glu Gln Arg Leu Ser Leu Gln Asp
                 85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
                115                 120                 125

Gln Leu Arg Val Tyr Lys Ala Pro Glu Glu Pro Asn Ile Gln Val Asn
            130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
                260                 265                 270

Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
            290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
            370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
                435                 440                 445

Asn Leu Ser Cys Glu Ala Ser Gly His Pro Arg Pro Thr Ile Ser Trp
            450                 455                 460

Asn Val Asn Gly Thr Ala Ser Glu Gln Asp Gln Asp Pro Gln Arg Val
465                 470                 475                 480
```

-continued

Leu Ser Thr Leu Asn Val Leu Val Thr Pro Glu Leu Glu Thr Gly
            485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
            530                 535                 540

Ser Thr Ser Thr Glu Arg Lys Leu Pro Glu Pro
545                 550                 555

<210> SEQ ID NO 12
<211> LENGTH: 556
<212> TYPE: PRT
<213> ORGANISM: Homo sapiens
<220> FEATURE:
<223> OTHER INFORMATION: CD146 sequence 5

<400> SEQUENCE: 12

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
290             295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
                355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                    405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
                435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
                515                 520                 525

Thr Thr Gly Leu Ser Thr Ser Thr Ala Ser Pro His Thr Arg Ala Asn
                530                 535                 540

Ser Thr Ser Thr Glu Arg Lys Leu Pro Glu Pro Glu
545                 550                 555

<210> SEQ ID NO 13
<211> LENGTH: 557
<212> TYPE: PRT
<213> ORGANISM: Homo sapiens
<220> FEATURE:
<223> OTHER INFORMATION: CD146 sequence 6

<400> SEQUENCE: 13

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
                35                  40                  45

Gly Leu Ser Gln Ser Gln Gly Asn Leu Ser His Val Asp Trp Phe Ser
                50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

-continued

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
        180                 185                 190

Ser Gln Thr Val Glu Ser Ser Gly Leu Tyr Thr Leu Gln Ser Ile Leu
    195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
        260                 265                 270

Leu Ala Asp Gly Asn Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
        340                 345                 350

Pro Glu Arg Gln Glu Gly Ser Ser Leu Thr Leu Thr Cys Glu Ala Glu
    355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
        420                 425                 430

Met Ala Phe Lys Glu Arg Lys Val Trp Val Lys Glu Asn Met Val Leu
    435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr

```
            515                 520                 525
Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser
545                 550                 555

<210> SEQ ID NO 14
<211> LENGTH: 558
<212> TYPE: PRT
<213> ORGANISM: Homo sapiens
<220> FEATURE:
<223> OTHER INFORMATION: CD146 sequence 7

<400> SEQUENCE: 14

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
```

```
                    325                 330                 335
Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg
545                 550                 555

<210> SEQ ID NO 15
<211> LENGTH: 21
<212> TYPE: DNA
<213> ORGANISM: Artificial Sequence
<220> FEATURE:
<223> OTHER INFORMATION: GAPDH Reverse Primer Sequence

<400> SEQUENCE: 15
ggtggtctcc tgacttcaac a                                           21

<210> SEQ ID NO 16
<211> LENGTH: 22
<212> TYPE: DNA
<213> ORGANISM: Artificial Sequence
<220> FEATURE:
<223> OTHER INFORMATION: GAPDH Forward Primer Sequence

<400> SEQUENCE: 16
gttgctgtag ccaattcgtt gt                                          22

<210> SEQ ID NO 17
<211> LENGTH: 21
<212> TYPE: DNA
<213> ORGANISM: Artificial Sequence
<220> FEATURE:
<223> OTHER INFORMATION: CD146 Reverse Primer

<400> SEQUENCE: 17
ggctaatgcc tcagatcgat g                                           21
```

```
<210> SEQ ID NO 18
<211> LENGTH: 23
<212> TYPE: DNA
<213> ORGANISM: Artificial Sequence
<220> FEATURE:
<223> OTHER INFORMATION: CD146 Forward Primer

<400> SEQUENCE: 18
aatatggtgt tgaatctgtc ttg                                              23
```